United States Patent [19]
Baxter et al.

[11] Patent Number: 5,508,270
[45] Date of Patent: Apr. 16, 1996

[54] NUCLEOSIDE PHOSPHINATE COMPOUNDS AND COMPOSITIONS

[75] Inventors: Anthony D. Baxter, Northwich; Eric K. Baylis, Stockport; Stephen P. Collingwood, Westhoughton; Roger J. Taylor, Stretford, all of England; Alain Mesmaeker, Kanerkinden; Chantal Schmit, Basel, both of Switzerland

[73] Assignee: Ciba-Geigy Corporation, Tarrytown, N.Y.

[21] Appl. No.: 203,962

[22] Filed: Feb. 28, 1994

[30] Foreign Application Priority Data

Mar. 6, 1993 [GB] United Kingdom ............... 9304620

[51] Int. Cl.$^6$ ............................................. A61K 31/70
[52] U.S. Cl. ................ 514/47; 514/48; 514/51; 536/26.1; 536/26.7; 536/26.8
[58] Field of Search ................. 536/25.34, 26.7, 536/26.8, 26.1; 514/47, 48, 51

[56] References Cited

FOREIGN PATENT DOCUMENTS

| 479640 | 4/1992 | European Pat. Off. |  |
|---|---|---|---|
| 477454 | 4/1992 | European Pat. Off. |  |
| 0479640 | 4/1992 | European Pat. Off. | 536/25.34 |
| 9119727 | 12/1991 | WIPO | 536/26.7 |
| 9213869 | 8/1992 | WIPO | 536/25.34 |

OTHER PUBLICATIONS

Tetrahedron Letters, vol. 28, No. 31, pp. 3623–3626, (1987).
Collection of Czechoslovak Chemical Communications, vol. 54, pp. 1055–1066, (1989).
Tetrahedron Letters, vol. 30, No. 19, pp. 2567–2570, (1989).
Chem. Abst. 69(9): 36381p (1968).
R. L. Whistler et al. Journal of Organic Chemistry vol. 33 No. 6, Jun. 1968 pp. 24.
Chem. Abst. vol. 99. No. 11, 88502t (1983).
Chem. abst. vol. 112, 36339N (1990).
Chem. abst. vol. 119, 96051s (1993).
H. Tanaka et al. Tetrahedron Letters vol. 30, No. 19 pp. 2567–2570 (1989).

Primary Examiner—Douglas W. Robinson
Assistant Examiner—James Oliver Wilson
Attorney, Agent, or Firm—George R. Dohmann

[57] ABSTRACT

A compound of formula

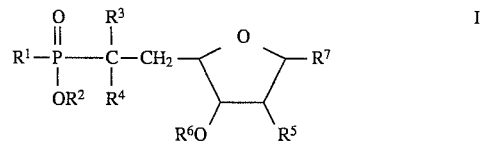

where
$R^1$ is hydrogen or a protecting group Q;
$R^2$ is hydrogen, a $C_1$–$C_8$ aliphatic radical, a $C_6$–$C_{15}$ aromatic radical, a $C_3$–$C_8$ cycloaliphatic radical, a $C_7$–$C_{13}$ araliphatic radical, an alkali metal ion or an ammonium ion;
$R^3$ and $R^4$ are independently hydrogen, halogen or hydroxy;
$R^5$ is $C_6$–$C_{10}$ aryloxythiocarbonyloxy, the $C_6$–$C_{10}$ aryl group being unsubstituted or substituted, or $R^5_a$;
$R^5_a$ is hydrogen, fluorine, chlorine, hydroxy, —$OR^8$, —$OCOR^8$ or silyloxy substituted by three $C_1$–$C_{15}$ hydrocarbyl groups;
$R^6$ is hydrogen, a $C_1$–$C_{10}$ aliphatic radical, a $C_6$–$C_{15}$ aromatic radical, a $C_7$–$C_{16}$ araliphatic radical, —$COR^9$, —$SO_2R^9$ or silyl substituted by three $C_1$–$C_{15}$ hydrocarbyl groups;
$R^7$ is a monovalent nucleoside base radical, hydroxyl, —$OR^8$ or —$OCOR^8$, and
$R^9$ are independently a $C_1$–$C_{10}$ aliphatic radical, a $C_3$–$C_8$ cycloaliphatic radical, a $C_6$–$C_{15}$ aromatic radical or a $C_7$–$C_{16}$ araliphatic radical; or
$R^5$ and the indicated $R^6O$-together denote an isopropylidenedioxy group or $R^5$ and $R^7$ together denote an isopropylidenedioxy group, provided that when $R^5$ and $R^7$ together denote isopropylidenedioxy, $R^1R^2$, $R^3R^4$ and $R^6$ are not all hydrogen. The disclosure further relates to a method of preparing the compounds of formula I by reacting a olefinic acetonide with a phosphinate compound and to the use of the compounds of formula I as pharmaceutical agents.

10 Claims, No Drawings

NUCLEOSIDE PHOSPHINATE COMPOUNDS AND COMPOSITIONS

This invention relates to mononucleotide analogues which are useful as intermediates in the synthesis of oligonucleotide analogues for use as anti-sense probes for inhibiting gene expression in biological systems. It also relates to intermediates for the mononucleotide analogues.

The compounds of the invention may themselves be useful as pharmaceuticals in the treatment of viruses such as influenza, herpes and HIV and in the treatment of diseases which are mediated through inhibition or activation of enzymes/receptors which recognise nucleotide $5^1$ monophosphates as substrates or ligands.

Accordingly, the present invention provides a compound of formula

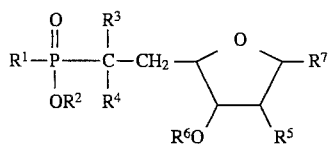   I where
$R^1$ is hydrogen or a protecting group Q;
$R^2$ is hydrogen, a $C_1$–$C_8$ aliphatic radical, a $C_3$–$C_8$ cycloaliphatic radical, a $C_6$–$C_{15}$ aromatic radical, a $C_7$–$C_{13}$ araliphatic radical, an alkali metal ion or an ammonium ion;
$R^3$ and $R^4$ are independently hydrogen, halogen or hydroxy;
$R^5$ is $C_6$–$C_{10}$ aryloxythiocarbonyloxy, the $C_6$–$C_{10}$ aryl group being unsubstituted or substituted, or $R^5_a$;
$R^5_a$ is hydrogen, fluorine, chlorine, hydroxy, —$OR^8$, —$OCOR^8$ or silyloxy substituted by three $C_1$–$C_{15}$ hydrocarbyl groups;
$R^6$ is hydrogen, a $C_1$–$C_{10}$ aliphatic radical, a $C_6$–$C_{15}$ aromatic radical, a $C_7$–$C_{16}$ araliphatic radical, —$COR^9$, —$SO_2R^9$ or silyl substituted by three $C_1$–$C_{15}$ hydrocarbyl groups;
$R^7$ is a monovalent nucleoside base radical, hydroxy, —$OR^8$ or —$OCOR^8$, and
$R^8$ and $R^9$ are independently a $C_1$–$C_{10}$ aliphatic radical, a $C_3$–$C_8$ cycloaliphatic radical, a $C_6$–$C_{15}$ aromatic radical or a $C_7$–$C_{16}$ araliphatic radical; or $R^5$ and the indicated $R^6O$ together denote an isopropylidenedioxy group or $R^5$ and $R^7$ together denote an isopropylidenedioxy group, provided that when $R^5$ and $R^7$ together denote an isopropylidenedioxy group, $R^1$, $R^2$, $R^3$, $R^4$, and $R^6$ are not all hydrogen.

Generally, in compounds of formula I,
$R^2$ is hydrogen, substituted or unsubstituted $C_1$–$C_8$ alkyl, $C_3$–$C_8$ cycloalkyl, $C_6$–$C_{15}$ aryl or $C_7$–$C_{13}$ aralkyl, an alkali metal ion or an ammonium ion;
$R^5$ as $R^5_a$ is hydrogen, fluorine, chlorine, hydroxy, $C_1$–$C_{10}$ alkoxy, $C_2$–$C_{10}$ alkenoxy, $C_6$–$C_{15}$ aryloxy, $C_7$–$C_{16}$ aralkyloxy, —$OCOR^8$ or silyloxy substituted by three $C_1$–$C_{15}$ hydrocarbyl groups;
$R^6$ is hydrogen, substituted or unsubstituted $C_1$–$C_{10}$ alkyl, $C_2$–$C_{10}$ alkenyl, $C_6$–$C_{15}$ aryl or $C_7$–$C_{16}$ aralkyl, —$COR^9$, —$SO_2R^9$ or silyl substituted by three $C_1$–$C_{15}$ hydrocarbyl groups; and
$R^8$ and $R^9$ are independently substituted or unsubstituted $C_1$–$C_{10}$ alkyl, $C_2$–$C_{10}$ alkenyl, $C_3$–$C_8$ cycloalkyl, $C_6$–$C_{15}$ aryl or $C_7$–$C_{16}$ aralkyl.

The compounds of formula I may be in the form of one of the possible isomers, for example as a diastereomer, an optical isomer, a racemate or a mixture thereof.

Preferred isomers are of formula

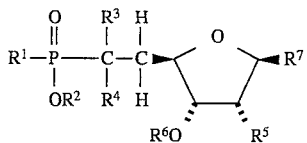   IA where $R^1$ to $R^7$ are as hereinbefore defined.

When $R^1$ is a protecting group Q, this may be any group which is known to be effective in protecting P—H bonds whilst reactions are carried out which would affect such bonds and be readily removable after such reactions to generate a P—H bond. Such protecting groups may be those in compounds of formula Ia of EP 0009348, or those in compounds described in Aust. J. Chem. 33, 292 (1980) or U.S. Pat. No. 4,933,478. Preferred protecting groups Q include those of formula

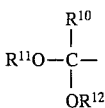   II where $R^{10}$ is hydrogen, $C_1$–$C_{10}$ alkyl, $C_3$–$C_8$ cycloalkyl, $C_6$–$C_{10}$ aryl or $C_7$–$C_{11}$ aralkyl and $R^{11}$ and $R^{12}$ are independently $C_1$–$C_{10}$ alkyl. Preferred groups of formula II are those where $R^{10}$ is hydrogen or $C_1$–$C_4$ alkyl and $R^{11}$ and $R^{12}$ are each $C_1$–$C_4$ alkyl. In especially preferred compounds, $R^1$ is hydrogen or a group of formula II where $R^{10}$ is hydrogen or methyl and $R^{11}$ and $R^{12}$ are each methyl or ethyl.

Other preferred protecting groups Q are those of formula

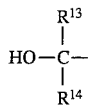   III where $R^{13}$ and $R^{14}$ are independently $C_1$–$C_{10}$ alkyl or $R^{13}$ is $C_1$–$C_{10}$ alkyl and $R^{14}$ is $C_6$–$C_{10}$ aryl. Preferred groups of formula III are those where $R^{13}$ and $R^{14}$ are each $C_1$–$C_4$ alkyl, especially that where $R^{13}$ and $R^{14}$ are each methyl.

$R^2$ as unsubstituted or substituted $C_1$–$C_8$ alkyl may be, for example, methyl, ethyl, n-propyl, isopropyl, n-butyl, isobutyl, tert-butyl, n-pentyl, neopentyl, n-hexyl, n-octyl or 2-ethylhexyl, preferably $C_1$–$C_6$ alkyl, particularly methyl, ethyl or isobutyl, or any of these groups substituted by $C_1$–$C_4$ alkoxy, halogen or cyano, for example methoxymethyl, 2-methoxyethyl, 2-ethoxyethyl, 2-butoxyethyl, 3-methoxypropyl, 4-methoxybutyl, 2-methoxybutyl, 2-fluoroethyl, 2,2,2-trifluoroethyl, 2-chloroethyl, 2-chloro-n-propyl, 3-chloro-n-butyl or, preferably, 2-cyanoethyl. $R^2$ as substituted or unsubstituted $C_7$–$C_{13}$ aralkyl may be, for example, benzyl, 4-methylbenzyl, o-methoxybenzyl, p-methoxybenzyl, diphenylmethyl, 2-phenylethyl, 2-phenylpropyl, or 3-phenylpropyl, preferably $C_7$–$C_9$ aralkyl, especially benzyl. $R^2$ as an alkali metal ion is preferably a sodium or potassium ion. $R^2$ as an ammonium ion may be an unsubstituted ammonium ion or a substituted ammonium ion, for example an alkylammonium ion such as a methylammonium, ethylammonium, n-propylammonium, isopropylammonium, n-butylammonium, isobutylammonium, tert-butylammonium, 2-hydroxyethylammonium or 3-hydroxypropylammonium, a dialkylammonium ion such as dimethylammonium, diethylammonium, di-(2-hydroxyethyl)ammonium, methyl (2-hydroxyethyl)ammonium, di-n-propylammonium, or di(isopropyl)ammonium or a trialkylammonium ion such as trimethylammonium, triethylammonium, methyldiethylammonium, tri-n-butylammonium or tri(2-hydroxyethyl)ammonium.

Preferably $R^2$ is hydrogen, unsubstituted or substituted $C_1$–$C_6$ alkyl, especially methyl, ethyl, isobutyl or 2-cyanoethyl, or unsubstituted or substituted ammonium, especially ammonium or triethylammonium.

$R^3$ and $R^4$ are preferably each hydrogen.

When $R^5$ denotes $C_1$–$C_{10}$ alkoxy it may be, for example, methoxy, ethoxy, n-propoxy, isopropoxy, n-butoxy, isobutoxy, tert-butoxy, n-pentoxy, neopentyloxy, n-hexyloxy, n-octyloxy, 2-ethylhexyloxy, n-nonyloxy or n-decyloxy. $R^5$ as alkoxy is preferably $C_1$–$C_4$ alkoxy, particularly methoxy or ethoxy.

$R^5$ as $C_2$–$C_{10}$ alkenoxy may be, for example, vinyloxy, allyloxy, 1-propenyloxy, isopropenyloxy, methallyloxy, 2-butenyloxy, 1-butenyloxy, isobutyloxy, pentenyloxy, hexenyloxy, octenyloxy or decenyloxy. Preferably, $R^5$ as alkenoxy is $C_3$ or $C_4$ alkenoxy, particularly allyloxy or methallyloxy.

When $R^5$ denotes $C_6$–$C_{15}$ aryloxy, it may be, for example, phenoxy, o-tolyloxy, m-tolyloxy, p-tolyloxy, 2,3-dimethylphenoxy, 2,4-dimethylphenoxy, 2,5-dimethylphenoxy, alpha-naphthyloxy or beta-naphthyloxy. $R^5$ as aryloxy is preferably $C_6$–$C_8$ aryloxy, particularly phenoxy.

$R^5$ as aralkyloxy may be, for example, benzyloxy, 4-methylbenzyloxy, 2-phenylethoxy, 2-phenylpropoxy, 3-phenylpropoxy or diphenylmethoxy. Preferably $R^5$ as aralkyloxy is $C_7$ to $C_9$ aralkyloxy, particularly benzyloxy.

$R^5$ as tri($C_1$–$C_{15}$ hydrocarbyl)-substituted silyloxy may be, for example, trialkylsilyloxy such as trimethylsilyloxy, triethylsilyloxy, tri-n-propylsilyloxy, tri-isopropylsilyloxy, tri-n-butylsilyloxy, tri-isobutylsilyloxy, tri-tert-butylsilyloxy, isopropyldimethylsilyloxy, tert-butyldimethylsilyloxy or 1,1,2,2-tetramethylethyldimethylsilyloxy (thexyldimethylsilyloxy), aryldialkylsilyloxy such as phenyldimethylsilyloxy, phenyldiethylsilyloxy, phenyldiisopropylsilyloxy or phenyl-diotert-butylsilyloxy, or alkyldiarylsilyloxy such as isopropyldiphenylsilyloxy or tert-butyldiphenylsilyloxy. Preferably $R^5$ as tri($C_1$–$C_{15}$ hydrocarbyl)-substituted silyloxy is $C_1$–$C_6$ alkyldi ($C_6$–$C_8$aryl)silyloxy, especially tert-butyldiphenylsilyloxy, or branched $C_2$–$C_{10}$ alkyl di ($C_1$–$C_4$ alkyl)silyloxy, especially thexyldimethylsilyloxy.

$R^5$ as substituted or unsubstituted $C_6$–$C_{10}$ aryloxythiocarbonyloxy may be, for example, substituted or unsubstituted phenyloxythiocarbonyloxy, preferably $C_1$–$C_4$ alkyl- or halogen- substituted phenyloxythiocarbonyloxy, especially p-tolyloxythiocarbonyloxy or pentafluorophenoxythiocarbonyloxy.

$R^6$, $R^8$ or $R^9$ as unsubstituted or substituted $C_1$–$C_{10}$ alkyl may be, for example, methyl, ethyl, n-propyl, isopropyl, nobutyl, isobutyl, tert-butyl, n-pentyl, neopentyl, n-hexyl, n-octyl, 2-ethylhexyl, or n-decyl or any of these groups substituted by halogen, hydroxy or nitro. Preferably, $R^6$, $R^8$ or $R^9$ as $C_1$–$C_{10}$ alkyl is $C_1$ to $C_4$ alkyl, particularly methyl or ethyl.

When $R^6$, $R^8$ or $R^9$ denotes unsubstituted or substituted $C_2$–$C_{10}$ alkenyl, it may be, for example, vinyl, allyl, 1-propenyl, isopropenyl, methallyl, 2-butenyl, 1-butenyl, isobutenyl, pentenyl, hexenyl, octenyl or decyl, or any of these groups substituted by halogen, hydroxy or nitro. $R^6$, $R^8$ or $R^9$ as $C_2$–$C_{10}$ alkenyl is preferably $C_3$ or $C_4$ alkenyl, particularly allyl or methallyl.

$R^2$, $R^6$, $R^8$ or $R^9$ as unsubstituted or substituted $C_6$–$C_{15}$ aryl may be, for example, phenyl, o-tolyl, m-tolyl, p-tolyl, o-xylyl, m-xylyl, p-xylyl, alpha-naphthyl or beta-naphthyl, or any of these groups substituted by halogen, hydroxy, $C_1$–$C_4$ alkoxy or nitro. Preferably, $R^2$, $R^6$, $R^8$ or $R^9$ as unsubstituted or substituted $C_6$–$C_{15}$ aryl is $C_6$–$C_{10}$ aryl, particularly phenyl, tolyl, nitrophenyl or naphthyl.

When $R^6$, $R^8$ or $R^9$ denotes substituted or unsubstituted $C_7$–$C_{16}$ aralkyl, it may be, for example, benzyl, 4-methylbenzyl, 2-phenylethyl, 2-phenylpropyl, 3-phenylpropyl or diphenylmethyl, or any of these groups substituted by halogen, hydroxy, $C_1$–$C_4$ alkoxy or nitro. Preferably, it is $C_7$ to $C_9$ aralkyl, particularly benzyl.

$R^6$ as tri($C_1$–$C_{15}$ hydrocarbyl)-substituted silyl may be, for example, trialkylsilyl such as trimethylsilyl, triethysilyl, tri-n-propylsilyl, tri-isopropysilyl, tri-n-butylsilyl, tri-isobutysilyl, tri-tert-butylsilyl, isopropyldimethylsilyl, tert.butyldimethylsilyl or thexyldimethylsilyl, aryldialkylsilyl such as phenyldimethylsilyl, phenyldiethylsilyl, phenyldiisopropylsilyl or phenyl di-tert-butylsilyl, or alkyldiarylsilyl such as isopropyldiphenylsilyl or tert-butyldiphenylsilyl. Preferably $R^6$ as tri($C_1$–$C_{15}$ hydrocarbyl)-substituted silyl is $C_1$–$C_6$ alkyldi($C_6$–$C_8$ aryl) silyl, especially tert-butyldiphenylsilyl, or branched $C_2$–$C_{10}$ alkyl di ($C_1$–$C_4$ alkyl) silyl, especially thexyldimethylsilyl.

When $R^2$, $R^8$ or $R^9$ denotes $C_3$–$C_8$ cycloalkyl, it may be, for example, cyclopropyl, cyclobutyl, cyclopentyl, methylcyclopentyl, cyclohexyl, methylcyclohexyl, dimethylcyclohexyl, cycloheptyl or cyclooctyl. Preferably $R^2$, $R^8$ or $R^9$ as $C_3$–$C_8$ cycloalkyl is $C_6$–$C_8$ cycloalkyl, particularly cyclohexyl.

$R^7$ as a monovalent nucleoside base radical may be a radical of a naturally occuring nucleoside base, such as adeninyl, cytosinyl, thyminyl, guaninyl or uracilyl, which may be unsubstituted or substituted, for example on an amino nitrogen atom by an acyl group such as acetyl, an aralkyl oxyalkyl group such as benzyloxymethyl or an aracyl group such as benzoyl, or nitrobenzoyl, or a synthetic analogue thereof. Suitable analogues of natural nucleoside bases include purines such as 2-methylthioadenine, 2-aminoadenine, 6-hyrdoxypurine and 2-amino-6-chloropurine, pyrimidines such as 5-fluorouracil, 5-chlorouracil, 5-bromouracil, dihydrouracil and 5-methylcytosine, and derivatives thereof with protecting groups on basic N atoms. Preferably $R^7$ as a monovalent nucleoside base radical is unsubstituted or substituted thyminyl, cytosinyl, guaninyl or adeninyl, especially thyminyl, N-benzyloxymethylthyminyl, N-(4-nitrobenzoyl)thyminyl, cytosinyl, N-acetylcytosinyl, N-benzoylcytosinyl, guaninyl, adeninyl or N-benzoyladeninyl.

In preferred compounds of formula I, $R^5$ is hydrogen, hydroxy, $C_1$–$C_4$ alkoxy, —$OCOR^8$ where $R^8$ is $C_1$–$C_{10}$ alkyl, or $C_1$–$C_4$ alkyl- or halogen-substituted phenyloxythiocarbonyloxy, especially hydrogen, hydroxy, methoxy, —$OCOCH_3$, or p-tolyloxythiocarbonyloxy, or $R^5$ together with $R^7$ denotes an isopropylidenedioxy group or $R^5$ together with $R^6O$— denotes an isopropylidenedioxy group;

$R^6$ is hydrogen, $C_7$–$C_9$ aralkyl, —$COR^9$ or —$SO_2R^9$ where $R^9$ is unsubstituted or substituted $C_1$–$C_4$ alkyl or $C_6$–$C_{10}$ aryl, or $C_1$–$C_6$ alkyldi ($C_6$–$C_8$aryl) silyl, especially hydrogen, benzyl, —$COR^9$ where $R^9$ is methyl, phenyl, 4-nitrophenyl or alpha-naphthyl, —$SO_2R^9$ where $R^9$ is methyl or p-tolyl, or tert-butyldiphenylsilyl, or $R^6$ together with the attached oxygen atom and $R^5$ denotes an isopropylidenedioxy group; and $R^7$ is hydroxy, —$COR^8$ where $R^8$ is $C_1$–$C_{10}$ alkyl, or an unsubstituted or substituted thyminyl, cytosinyl, guaninyl, or adeninyl group, especially hydroxy, —$OCOCH_3$, thyminyl, N-benzyloxymethylthyminyl, adeninyl, cytosinyl, N-acetylcytosinyl, N-benzoylcytosinyl, guaninyl,N-(4-nitrobenzoylthyminyl, or N-benzoyladeninyl, or $R^7$ together with $R^5$ denotes an isopropylidenedioxy group.

Especially preferred compounds of the invention are those of formula I, particularly the stereoisomers of formula IA, in which (A) $R^1$ is hydrogen or a protecting group Q of formula II in which $R^{10}$ is hydrogen or methyl and $R^{11}$ and $R^{12}$ are each ethyl;

$R^2$ is hydrogen, methyl or ethyl; $R^3$, and $R^4$ and $R^5$ are each hydrogen; $R^6$ is hydrogen, —$COR^9$ where $R^9$ is phenyl, 4-nitrophenyl or alpha-naphthyl, —$SO_2R^9$ where $R^9$ is methyl or p-tolyl, or tert-butyldiphenylsilyl, and $R^7$ is thyminyl or N-(4-nitrobenzoyl)thyminyl; or $R^8$ and $R^7$ together denote an isopropylidenedioxy group.

(B) $R^1$ is hydrogen or a protecting group Q of formula III in which $R^{13}$ and $R^{14}$ are each methyl;

$R^2$ is hydrogen, methyl, ethyl, isobutyl or an ammonium or triethylammonium ion;

$R^3$ and $R^4$ are each hydrogen;

$R^5$ is hydrogen, hydroxy, methoxy, —$OCOCH_3$ or p-tolyloxythiocarbonyloxy;

$R^6$ is hydrogen, benzyl or —$COR^9$ where $R^9$ is methyl or 4-nitrophenyl; and $R^7$ is hydroxy, —$OCOCH_3$, thyminyl, N-benzyloxymethylthyminyl, cytosinyl, N-acetylcytosinyl, N-benzoylcytosinyl, guaninyl, adeninyl or N-benzoyladeninyl; or $R^5$ and $R^7$ together denote an isopropylidenedioxy group or $R^5$ together with $R^6O$— denotes an isopropylidenedioxy group.

Compounds of formula I, in which $R'$ is a protecting group Q, $R^2$ is $R^2a$— an unsubstituted or substituted $C_1$-$C_{10}$ alkyl, $C_3$-$C_8$ cycloalkyl or $C_7$-$C_{13}$ aralkyl group as hereinbefore described, and $R^7$ is a monovalent nucleoside base radical, may be prepared by reacting an oxetane of formula

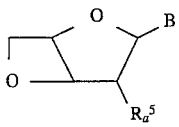   IV where B is a monovalent nucleoside base radical and $R^5_a$ is as hereinbefore defined, with an organometallic compound of formula

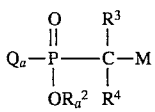   V where $R^2a$, $R^3$ and $R^4$ are as hereinbefore defined, $Q_a$ is a group of formula II, and M is lithium or magnesium, in the presence of a Lewis acid and, optionally, where a compound where $R^6$ is other than hydrogen is required, reacting the resulting product with either a compound of formula $R^6aX$   VI or a compound of formula

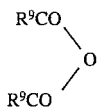   VII where $R^6a$ is the same as $R^6$ as hereinbefore defined except that $R^6a$ cannot be hydrogen, $R^9$ is as hereinbefore defined and X is a halogen atom or a hydroxyl group.

The reaction between the oxetane of formula IV and the organometallic compound is preferably carried out in the presence of a boron trifluoride complex as the Lewis acid. The reaction is usually carried out at low temperature, preferably from −120° C. to 40° C., in an organic solvent, e.g. tetrahydrofuran, a hydrocarbon such as hexane or a mixture thereof, using 1 to 10 equivalents, preferably 4 to 6 equivalents, of the organometallic compound per equivalent of the oxetane. The organometallic compound of formula V is preferably formed in situ by reaction of an organolithium, preferably an alkyllithium, or an organomagnesium halide, preferably an alkylmagnesium halide, with a compound of formula

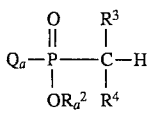   VIII where $Q_a$, $R^3$, $R^4$ and $R^2a$ are as hereinbefore defined. A suitable procedure for reaction of a nucleoside oxetane with an organometallic compound is described in H. Tanaka et al. Tetrahedron Lett., 30,2567 (1989).

Oxetanes of formula IV may be prepared by reaction of a compound of formula

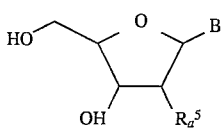   IX where B and $R^5_a$ are as hereinbefore defined, with methane sulphonyl chloride in pyridine, followed by treatment with aqueous sodium hydroxide, using the procedure of J. P. Horwitz et al, J. Org. Chem., 31,205 (1966).

Compounds of formula VIII can be obtained by reaction of a protected phosphinate ester of formula

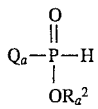   X where $Q_a$ and $R^2a$ are as hereinbefore defined, with a compound of formula

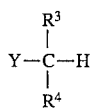   XI where $R^3$ and $R^4$ are as hereinbefore defined and Y denotes a leaving atom or group.

Phosphinate esters of formula X may be prepared by known methods, for example as described in EP 0009348, Aust. J. Chem. 33, 212 (1980) or U.S. Pat. No. 4,933,478.

The leaving atom or group Y in formula XI may be, for example, a halogen atom or a residue of an organic acid after removal of an acidic hydrogen atom therefrom, such as an organic sulphonate group, e.g. a p-toluenesulphonate or trifluoromethanesulphonate group. Preferably Y is a halogen atom or an arylsulphonate group, especially a chlorine or bromine atom or a p-toluenesulphonate group. Thus compounds of formula XI are known or may be prepared by known methods.

The reaction between the protected phosphinate ester of formula X and the compound of formula XI may be carried out under conventional conditions for substitution reactions at a P—H bond, for example using a base such as sodium, sodium hydride or an alkyllithium in an inert organic solvent such as tetrahydrofuran.

Compounds of formula IX where $R^5_a$ is hydrogen or hydroxy are readily available nucleosides. Compounds of formula IX where $R^5_a$ is other than hydrogen and hydroxy can be prepared by conventional halogenation, etherification, esterification or silylation reactions of compounds where $R^5_a$ is hydroxy.

The product of the reaction of the oxetane of formula IV and the organometallic compound of formula V is a compound of formula

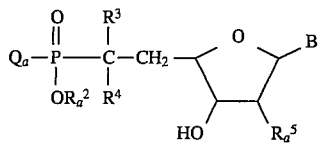   XII where $Q_a$, B, $R^2a$, $R^3$, $R^4$ and $R^5_a$ are as hereinbefore defined. Reaction of this compound with a compound of formula VI or VII may be effected using conventional esterification or etherification procedures. Thus, where $R^6$ is a group —$COR^9$, where $R^9$ is as hereinbefore defined, esterification may be carried out by reaction of the compound of formula XII with an acid of formula $R^9$ COOH, or the acid chloride or anhydride thereof, in an organic solvent such as an aromatic hydrocarbon, or tetrahydrofuran or a mixture thereof, in the presence of an esterification catalyst. When, as in preferred embodiments of the invention, it is desired to invert the stereochemical orientation of the hydroxy group in the compound of formula V, esterification may be effected using the procedure of Mitsunobu (Synthesis 1981, 1) in the presence of a triarylphosphine and an azodicarboxylate such as diethyl azodicarboxylate or diisopropyl azodicarboxylate.

The compounds of formula VI are alkyl halides, alkenyl halides, aryl halides, aralkyl halides, carboxylic acids, carboxylic acid halides sulphonic acids, sulphonyl halides or trialkylsilyl halides which are either available commercially or may be prepared by known methods. The compounds of formula VII are carboxylic acid anhydrides which are either available commercially or obtainable by known methods.

The reaction of the oxetane of formula IV with the organometallic compound of formula V is particularly suitable for the preparation of compounds of formula I where Q is a group of formula II, $R^2$ is methyl or ethyl and $R^3$, $R^4$ and $R^5$ are each hydrogen.

Compounds of formula I where $R^1$ is a protecting group Q, $R^2$ is $R^2a$ as hereinbefore defined, $R^3$ and $R^4$ are each hydrogen, and $R^5$ and $R^7$ together denote an isopropylidenedioxy group may be prepared by reacting an olefinic acetonide of formula

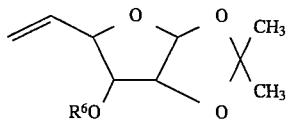   XIII where $R^6$ is as hereinbefore defined, with a phosphinate of formula

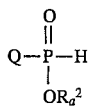   XIV where Q and $R^2a$ are as hereinbefore defined, in the presence of a free radical initiator. Suitable initiators include azo compounds such as azobis(isobutyronitrile), peroxides such as benzoyl peroxide, tert-butyl peroxide or 2,2-bis (tert-butylperoxy)propane, peresters such as tert-butyl perbenzoate or tert-butyl per-2-ethylhexanoate, percarbonates such as diacetyl perdicarbonate or bis(4-tert-butylcyclohexyl)perdicarbonate or persalts such as potassium persulphate. The initiator is generally used in an amount of 0.1 to 100 mol %, preferably 5 to 15, mol %, per mol of the olefinic compound of formula XIII.

The reaction between the olefinic acetonide and the phosphinate may be carried out without a solvent, but is preferably carried out in an organic solvent, usually an aromatic hydrocarbon such as benzene, toluene or xylene. It may be carried out at temperatures of 30° to 100° C., preferably 70° to 90° C.

The olefinic acetonide may be prepared from a diacetonide of formula

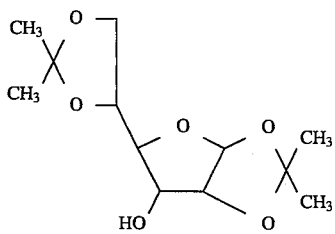   XV which itself can be prepared as described in Carbohyd. Res. 24 (1972) 194-5. The diacetonide may be reacted with a compound of formula VI or VII to etherify or esterify the hydroxyl group and the product reacted with 80% acetic acid at ambient temperature to give a monoacetonide of formula

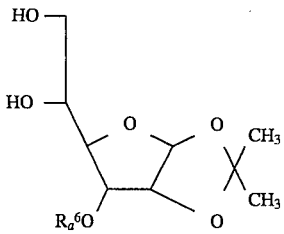   XVI where $R^6_a$ is as hereinbefore defined, which is then reacted with methanesulphonyl chloride in the presence of a base to replace both the indicated hydroxyl groups by methane sulphonyloxy groups. The product is reacted with sodium iodide in methyl ethyl ketone at 70°–90° C. to give an olefinic acetonide of formula

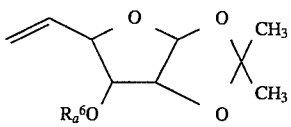   XVII which can be hydrolysed by treatment with potassium carbonate in aqueous methanol at ambient temperature to give an olefinic acetonide of formula XIII where $R^6$ is hydrogen.

The phosphinate of formula XIV where Q is a group of formula III may be prepared by esterifying a phosphonous acid of formula

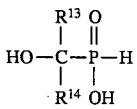   XVIII with an alcohol of formula $R^2a$ OH, where $R^2a$, $R^{13}$ and $R^{14}$ are as hereinbefore defined.

The esterification may be carried out at −20° to 30° C., preferably 0° to 10° C. It is conveniently carried out in a solvent, preferably an ether such as tetrahydrofuran, preferably in the presence of a base, usually a tertiary amine such as dimethylaminopyridine, and a dehydrating agent such as $N,N^1$-dicyclohexylcarbodiimide.

Phosphonous acids of formula XVIII can be prepared by reacting hypophosphorous acid with a ketone of formula

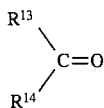   XIX where $R^{13}$ and $R^{14}$ are as hereinbefore defined, or by reacting hypophosphorous acid with a ketal of this ketone using the procedure described by S. J. Fitch, J. Amer. Chem. Soc. 86, 61(1964), followed by hydrolysis of the resulting phosphonous ester, for example by heating with water.

The phosphinate of formula XIV where Q is a group of formula II is a phosphinate of formula X which can be obtained as hereinbefore described.

The product of reaction between the olefinic acetonide of formula XIII and the phosphinate of formula XIV is a compound of formula I which is also a compound of formula

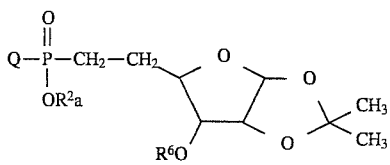   XX where Q, $R^2a$ and $R^6$ are as hereinbefore defined.

Compounds of formula XX may be converted into compounds of formula I where $R^5$ and $R^7$ are each hydroxy by reaction with a hydrolysing agent for the acetonide group, for example an acidic ion exchange resin, to give a compound of formula

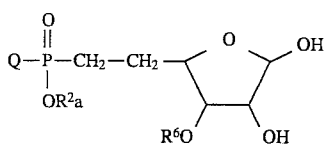   XXI where Q, $R^2a$ and $R^6$ are as hereinbefore defined.

Compounds of formula XXI may be converted, by esterification with an acid of formula $R^8COOH$ or an anhydride or acyl halide thereof, where $R^8$ is as hereinbefore defined, into compounds of formula I where $R^8$ and $R^7$ are each —$OCOR^8$, i.e. compounds of formula

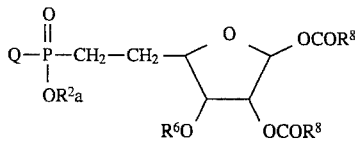   XXII where Q, $R^2a$, $R^6$ and $R^8$ are as hereinbefore defined.

These compounds may be converted, by glycosylation with a base of formula

BH   XXIII where B is a monovalent nucleoside base radical, into compounds of formula I where $R^7$ is a monovalent base radical, i.e. compounds of formula

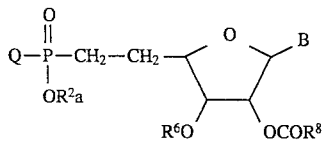   XXIV where B, Q, $R^2a$, $R^6$ and $R^8$ are as hereinbefore defined. This reaction may be carried out using known glycosylation procedures, for example in the presence of a silylating agent such as trimethylsilyl chloride, bis(trimethylsilyl)acetamide or hexamethyldisilazane and a catalyst such as a fluoralkanesulphonate salt in an organic solvent such as acetonitrile or 1,2-dichloroethane at a temperature of 40°–90° C. followed, where Q is a group of formula III, by treatment with an aqueous acid, usually an organic acid such as acetic acid, to regenerate the tertiary hydroxyl group which has become silylated during the glycosylation reaction.

The bases of formula XXIII are readily available nucleoside bases such as adenine, cytosine, guanine, thymine or uracil or substituted derivatives or analogues thereof prepared by known procedures.

Compounds of formula I in which $R^5$ is hydroxy, $R^6$ is hydrogen and $R^7$ is a monovalent nucleoside base radical can be prepared by subjecting a compound of formula XXIV where $R^6$ is —$COR^9$ or —$SO_2R^9$ to mild basic hydrolysis, for example by treatment with potassium carbonate in methanol at ambient temperature, to hydrolyse the —$OCOR^8$ group and the —$OCOR^9$ or —$SO_2R^9$ group.

Compounds of formula I where $R^1$ is a protecting group Q, and $R^5$ and $R^6O$— together denote an isopropylidenedioxy group can be prepared by reacting a compound of formula I in which $R^5$ is hydroxy, $R^6$ is hydrogen and $R^7$ is a monovalent nucleoside base radical with 2,2-dimethoxypropane in the presence of an acid catalyst such as p-toluenesulphonic acid. The reaction may be carried out at 60° to 120° C., preferably 95° to 105° C.

Compounds of formula I where $R^1$ is a protecting group Q, $R^2$ is $R^2a$, $R^3$ and $R^4$ are each hydrogen and $R^7$ is a monovalent nucleoside base radical B can also be prepared by reacting an olefinic nucleoside of formula

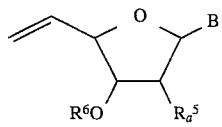   XXV where B, $R^5_a$ and $R^6$ are as hereinbefore defined with a phosphinate of formula XIV in the presence of a free radical initiator, for example under the same conditions as used for the reaction of the phosphinate with the olefinic acetonide of formula XIII.

Olefinic nucleosides of formula XXV where $R^5_a$ is —$OCOR^8$ may be obtained by glycosylation of a compound of formula

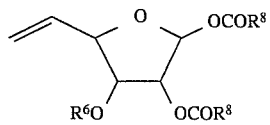   XXVI where $R^6$ and $R^8$ are as hereinbefore defined, with a base of formula XXIII, for example under the conditions hereinbefore, described for glycosylation of compounds of formula XXII.

Compounds of formula XXV where $R^5_a$ is hydroxy can be prepared by hydrolysis of compounds of formula XXV where $R^5_a$ is —$OCOR^8$. The resulting compounds can be etherified using conventional etherification procedures to give compounds of formula XXV where $R^5_a$ is —$OR^8$, where $R^8$ is as hereinbefore defined, or converted by conventional nucleophilic substitution reactions into compounds of formula XXV where $R^5_a$ is fluorine or chlorine, or deoxygenated using known deoxygenation procedures such as those described by Hartwig, Tetrahedron 39,2609 (1983), to give compounds of formula XXV where $R^5_a$ is hydrogen.

Compounds of formula XXVI can be prepared by reaction of the olefinic acetonide of formula XVII with an acidic ion exchange resin to hydrolyse the acetonide group to form a compound of formula

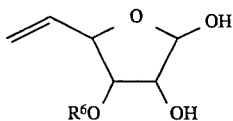   XXVII where $R^6$ is as hereinbefore defined, and esterifying the hydroxyl groups in this compound by reaction with an acid of formula $R^8COOH$ or an anhydride or acid halide thereof, where $R^8$ is as hereinbefore defined, to give a compound of formula XXVI.

Compounds of formula XX where Q is a group of formula II and $R^6$ is hydrogen can also be prepared by reacting a compound of formula

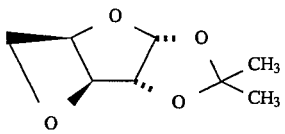   XXVIII with an organometallic compound of formula V, in the presence of a Lewis acid, preferably under conditions hereinbefore described for reaction of oxetanes of formula IV with organometallic compounds of formula V, to give compounds of formula

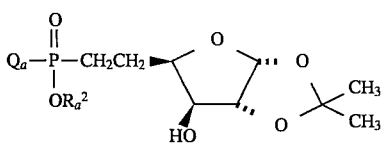   XXIX where $Q_a$ and $R^2_a$ are as hereinbefore defined. The compounds of formula XXVIII can be prepared by the method of J. P. Horwitz et al, J. Org. Chem. 28,942 (1963).

Compounds of formula XXIX can be oxidised, for example by a Swern oxidation using dimethyl sulphoxide and oxalyl chloride in the presence of a base such as triethylamine, to a mixture of a novel ketone of formula

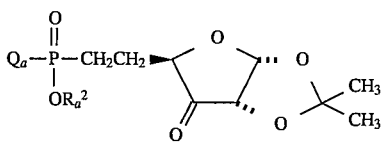   XXX and its novel hydration product of formula

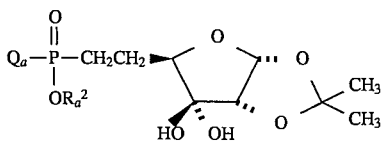   XXXI where $Q_a$ and $R^2a$ are as hereinbefore defined.

The mixture can be reduced, for example by reaction with a metal borohydride, to a compound of formula

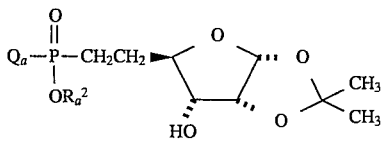   XXXII where $Q_a$ and $R^2a$ are as hereinbefore defined, which is a compound of formula I where $R^1$ is $Q_a$, $R^2$ is $R^2a$, $R^3$ and $R^4$ are hydrogen, $R^6$ is hydrogen and $R^5$ and $R^7$ together denote an isopropylidenedioxy group, and is the same as the compound of formula XXIX except that the position of the hydroxy group has been inverted.

Compounds of formula I in which $R^1$ is hydrogen may be prepared by hydrolysis of compounds of formula I where $R^1$ is a protecting group Q, and $R^2$ is $R^2a$ as hereinbefore defined, to replace Q by a hydrogen atom and, optionally, to replace $R^2a$ by a hydrogen atom. When Q is a group of formula II, hydrolysis may be effected by reaction with a trialkylsilyl halide such as trimethylsilyl chloride, trimethylsilyl bromide or trimethylsilyliodide. This reaction may be carried out at a temperature of −30° C. to 100° C., preferably 0° to 40° C., in an inert organic solvent, for example a halohydrocarbon such as chloroform or trichloroethane, an ether such as tetrahydrofuran or an aromatic hydrocarbon such as benzene, toluene or xylene, or a mixture of two or more of such solvents in the presence of, or followed by the addition of an alcohol such as ethanol. In general, when the desired product is a compound of formula I in which $R^1$ and $R^2$ are hydrogen, a trialkylsilyl iodide is used, while when a compound of formula I in which $R^1$ is hydrogen and $R^2$ is $R^2a$ as hereinbefore defined is desired, a trialkylsilyl chloride is used. When a trialkylsilyl bromide is used, a mixture of a compound where $R^1$ is hydrogen and $R^2$ is $R^2_a$ and a compound where $R^1$ and $R^2$ are each hydrogen is generally obtained.

When Q is a group of formula III, hydrolysis can be effected under basic conditions, for example by treatment with aqueous ammonia at 70°–90° C., which gives a compound of formula I where $R^1$ is hydrogen and $R^2$ is an ammonium ion, which on acidification gives a compound where $R^1$ and $R^2$ are hydrogen. Compounds of formula I where $R^1$ is hydrogen and $R^2$ is an alkali metal or a substituted ammonium ion can be prepared by carrying out such hydrolysis with an alkali or by reacting a compound of formula I where $R^1$ and $R^2$ are both hydrogen with an alkali metal base or an amine to form a salt.

Compounds of formula I in which $R^1$ and $R^2$ are hydrogen can also be prepared by base hydrolysis of a compound of formula I where $R^1$ is hydrogen and $R^2$ is $R^2a$, for example by treatment with alkali in an alcohol at a temperature from ambient to reflux temperature. If $R^5$ is $-OCOR^8$ or $R^6$ is $-COR^9$ in the compound treated with base, these groups will also be hydrolysed, to hydroxyl groups, by such treatment.

Hydrolysis of compounds of formula I where $R^1$ is Q, to replace Q by a hydrogen atom, can also be effected by treatment with an acid under hydrolytic conditions. It may be carried out with a mineral acid such as hydrochloric acid, in which case $R^2$ in the resulting compound is hydrogen, or with an organic acid such as acetic acid, in which case the resulting product may be a compound where $R^2$ is $R^2_a$, a compound where $R^2$ is hydrogen or a mixture thereof.

Compounds of formula I where $R^5$ is hydrogen can be prepared from compounds of formula I where $R^5$ is hydroxy by conventional deoxygenation methods, for example by reaction with an unsubstituted or substituted $C_6$–$C_{10}$ aryloxythiocarbonyl halide, such as p-tolylchlorothionoformate or pentafluorophenylchlorothionoformate, to form compounds of formula I where $R^5$ is an unsubstituted or substituted $C_6$–$C_{10}$ aryloxythiocarbonyloxy group, and then removing this group by reaction with a trialkylstannane such as tri-n-butylstannane in the presence of a free radical initiator such as those hereinbefore described. This and other methods for the deoxygenation of alcohols are described by Hartwig, Tetrahedron 39,2609 (1983).

When mixtures of diastereomers of compounds of formula I, or intermediates therefor, are obtained, these can be separated by known methods, for example by fractional distillation, crystallisation or chromatography.

Compounds of formula I as hereinbefore described can be used as intermediates in the preparation of oligonucleotide analogues, which can be used in the treatment of diseases modulated by proteins, and dinucleotide analogues and oligonucleotide analogues which can be used in the treatment of viruses such as influenza, herpes and HIV.

For example, a compound of formula I, where $R^1$ is H, $R^2$ is ethyl, $R^3$, $R^4$ and $R^5$ are hydrogen, $R^6$ is benzoyl and $R^7$ is 1-thyminyl, can be reacted with an aldehyde of formula

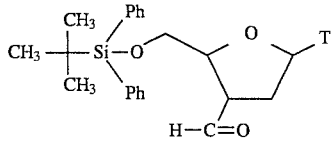
XXXIII where Ph is phenyl and T is 1-thyminyl, in the presence of a base, preferably a non-nucleophilic base, to form a dinucleotide analogue of formula

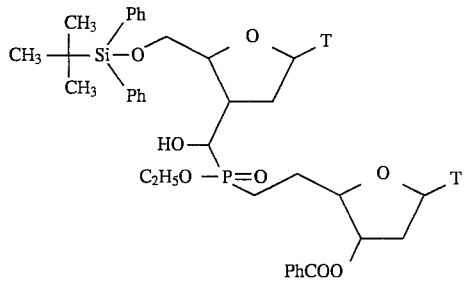
XXXIV which gives, after removal of the indicated hydroxyl group by a conventional deoxygenation reaction, a dinucleotide analogue having anti-viral activity. The dinucleotide analogues can be incorporated in oligonucleotide analogues by standard automated DNA synthesis.

Accordingly, the present invention also provides the use of a compound of formula I as hereinbefore defined in the synthesis of dinucleotide analogues or oligonucleotide analogues.

Compounds of formula I can themselves be used in the treatment of viruses such as those mentioned above. Accordingly, the present invention also provides a pharmaceutical composition comprising as active ingredient a compound of the invention as hereinbefore described. Optimum dosages and treatment schedules can readily be determined by those skilled in the art. It will generally be preferred to administer therapeutic agents in accordance with the invention internally, for example orally, by inhalation, intraveneously or intramuscularly. Other methods of administration, such as transdermal, topical or intra-lesional methods and by inclusion in suppositries, can also be useful. Use in conjunction with pharmacologically acceptable careers is preferred for some therapeutic treatments.

The invention is illustrated by the following Examples.

Compounds used in the Examples are prepared as follows:

Methyl (1-hydroxy-1-methylethyl)phosphinate

Commercial hypophosphorous acid (50%) is concentrated to 94% on a rotary evaporator. A mixture of hypophosphorous acid (94%, 210.6 g, 3M) and 2,2-dimethoxypropane (917 g, 8.8M) is allowed to stand at room temperature for 6 days. The mixture is evaporated under vacuum and distilled on a wiped-wall still to give methyl(1-hydroxy-1-methylethyl)phosphinate (268 g, 65%, b.p. 65° C./0.1 mm).

$^{31}P$ nmr (CDCl$_3$, 24.15 MHZ) $\delta$=45 ppm, $J_{PH}$545 Hz. (Fitch. J. Amer. Chem. Soc. 1964, 86, 61).

Isobutyl (1-hydroxy-1-methylethyl)phosphinate

The methyl (1-hydroxy-1-methylethyl)phosphinate prepared as described immediately above is heated with water (1l) on a steam bath for 8 hours until conversion to 1-hydroxy-1-methylethylphosphonous acid is complete (monitored by $^{31}P$ nmr). The water is removed on a rotary evaporator and the residue is completely dried by co-evaporation with toluene. A sample of this phosphonous acid (4.6 g, 0.037M), isobutyl alcohol (3.02 g, 0.041M) and dimethylaminopyridine (0.5 g, 0.0041M) is stirred at 5° C. in tetrahydrofuran. Dicyclohexylcarbodiimide (8.4 g, 0.041M) is added portionwise over 30 minutes. On completion of the reaction ($^{31}P$ nmr), ether (50 ml) is added and the precipitated dicyclohexyl urea is filtered off.

Evaporation of the ether liquors gives a pale yellow oil (6.7 g) which is purified by chromatography on silica using ether, then ethyl acetate, as eluant to give isobutyl(1-hydroxy-1-methylethyl)phosphinate (4 g, 60%).

Found: C 47.0, H 9.5, P 17.1%; $C_7H_{17}O_3P$ requires C 46.7, H 9.5, P 17.2%.

$^{31}P$ nmr (CDCl$_3$, 162 MHZ) $\delta$=42.2 ppm.

Example 1

This example describes the preparation of the compound of formula

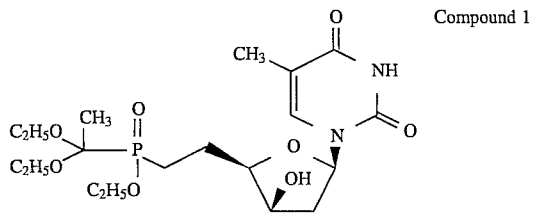
Compound 1

To a solution of ethyl methyl(1,1-diethoxyethyl)phosphinate (59.5 g, 0.26 mole) in tetrahydrofuran (THF) (500 ml) at −78° C. under an atmosphere of argon is added nBuLi (170 ml, 1.6 molar solution in hexanes) slowly over 20 minutes. The resulting solution is stirred at −78° C. for 90 minutes. Boron trifluoride etherate (39 g, 0.27 mole) is then added over 5 minutes followed after a further 5 minutes by the dropwise addition of a solution of 1-(3,5-anhydro-β-D-threo-pentofuranosyl)thymine (12 g, 53 mmole) in THF (500 ml) over one hour. The resulting solution is stirred for one hour at −78° C. before the addition of NaHCO$_3$ (saturated) solution (30 ml) plus NaHCO$_3$ (10 g). The resulting mixture is allowed to warm to room temperature over a few hours and then concentrated in vacuo. Addition of dichloromethane (400 ml) and filtration gives a clear yellow oil after concentration. Purification by vacuum flash silica chromatography gradient elution (chloroform-chloroform/ethanol 15: 1) gives Compound 1 as a hygroscopic white solid, mp 24°–51° C.

Found C 49.7%, H 7.4%, N 6.0%, P 6.7%; required for $C_{19}H_{33}N_2O_8$ P.½H$_2$O, C 49.9%, H 7.5% N 6.1%, P 6.75%.

NMR characterisation as a mixture of 2-diastereoisomers:

$^{31}P$ nmr $^1H$ decoupled (CDCl$_3$, 36.4 MHz) $\delta$50.7, 50.5 ppm.

Example 2

This Example describes the preparation of the compound of formula

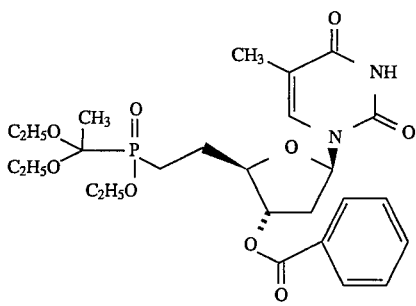

Compound 2

Diethylazodicarboxylate (2.8 ml, 18 mmole) is added dropwise to a cooled (0°–5° C.) solution of Compound 1 (7.3 g, 16.3 mmole), triphenylphosphine (4.7 g, 18 mmole) and benzoic acid (2.19 g, 18 mmole) in a mixture of toluene (100 ml) and tetrahydrofuran (30 ml) under argon. After standing at room temperature for 60 hours, the mixture is concentrated and purified by vacuum flash chromatography (gradient elution dichloromethane/ethanol 100:0→10:1) to give a white solid which is dissolved in dichloromethane (200 ml) and washed with saturated sodium hydrogen carbonate solution (5×100 ml), dried over magnesium sulphate and concentrated to give a white foam of Compound 2.

Found: C 55.9, H 7.0, N 4.8, P 5.8%; $C_{26}H_{37}N_2O_9P \cdot \frac{1}{2}H_2O$ requires C 55.6, H 6.8, N 5.0, P 5.5%.

NMR characterisation as a mixture of 2-diastereomers at phosphorus:

$^{31}P$ nmr $^1H$ decoupled (CDCl$_3$, 161.9 MHz) $\delta$49.1, 49.2 ppm.

Example 3

This Example describes the preparation of the compound of formula:

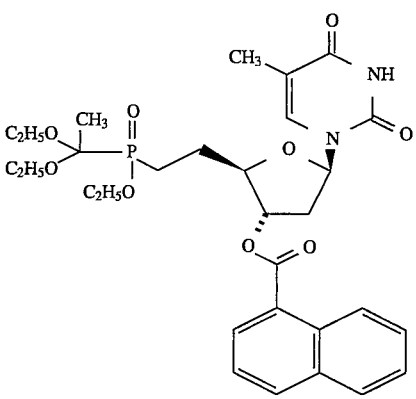

Compound 3

Diethylazodicarboxylate (2.1 ml, 13 mmole) is added dropwise (5 minutes) to a cooled (0°–5° C.) and stirred solution of Compound 1 (5 g, 11 mmole), triphenylphosphine (3.5 g, 13 mmole) and 1-naphthoic acid (2.3 g, 13 mmole) in a mixture of toluene (60 ml) and tetrahydrofuran (15 ml) under argon. The resulting solution is allowed to stand at room temperature for 48 hours and then concentrated in vacuo. Purification by flash silica column chromatography (eluant: chloroform/ethanol 50:1) gives Compound 3 as a white solid.

Found C 59.5%, H 6.8%, N 4.6%, P 5.3%; $C_{30}H_{39}N_2O_9P$ requires C 59.8%, H 6.5%, N 4.65%, P 5.15%.

NMR characterisation as a 1:1 mixture of diastereoisomers at phosphorus:

$^{31}P$ nmr $^1H$ decoupled (CDCl$_3$, 36.4 MHz) $\delta$48.3, 48.2 ppm.

Example 4

This example describes the preparation of the compound of formula

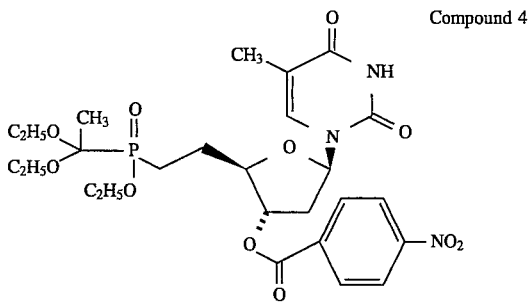

Compound 4

Diethylazodicarboxylate (0.42 ml, 2.7 mmole) is added dropwise (5 minutes) to a stirred solution of Compound 1 (1.0 g, 2.2 mmole), triphenylphosphine (0.70 g, 2.7retool) and p-nitrobenzoic acid (0.45 g, 2.7 mmole), in a mixture of toluene (20 ml) and tetrahydrofuran (5 ml) under argon. After standing at room temperature overnight the mixture is concentrated and purified by flash silica column chromatography, (eluant: chloroform/ethanol 50:1) to give Compound 4, mp 60°–63° C. Found C 52.3%, H 6.1%, N 6.8%, P 5.2%; required for $C_{26}H_{36}N_3O_{11}P$, C 52.25%, H 6.05%, N 7.05%, P 5.2%.

NMR characterisation as a 1:1 mixture of diastereoisomers at phosphorus:

$^{31}P$ nmr $^1H$ decoupled (CDCl$_3$, 36.4 MHz) $\delta$47.9, 47.2 ppm.

Example 5

This example describes the preparation of the compound of formula

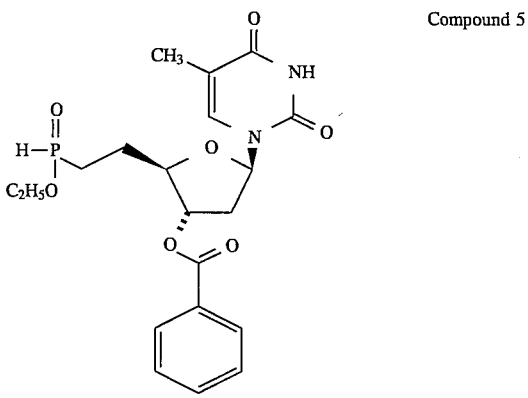

Compound 5

Trimethylsilylchloride (4.56 ml, 36 mmole) is added dropwise (2 minutes) at 0° C. to a stirred solution of Compound 2 (2 g, 3.6 mmole) and ethanol (1 ml) in chloroform (20 ml) under argon. The resulting solution is allowed to stand at room temperature overnight and then concentrated in vacuo to give an off-white foam which is purified by flash silica chromatography (eluant 40:1 chloroform/ethanol) to give Compound 5 as a white solid.

Found: C 52.7%: H 5.7%, N 6.1%, P 6.8%; $C_{20}H_{25}N_2O_7P.H_2O$ requires C 52.85%, H 6.0%, N 6.15%, P 6.8%.

NMR characterisation as a 1:1 mixture of diastereoisomers at Phosphorus:

$^{31}P$ nmr $^1H$ decoupled (162 MHz, $CDCl_3$) δ37.4, 37.1 ppm.

Example 6

This example describes the preparation of the compound of formula:

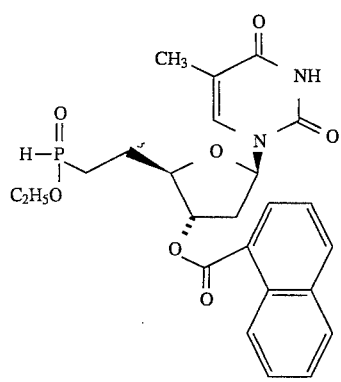

Compound 6

Trimethylsilylchloride (0.42 ml, 3.3 mmole) is added to a stirred solution of Compound 3 (199 mg, 0.33 mmole) in chloroform (5 ml) containing ethanol (10 pipette drops) under argon. The resulting solution is allowed to stand at room temperature overnight and then concentrated in vacuo to give an off-white foam which is purified by flash silica column chromatography (eluant 40:1 chloroform/ethanol) to give Compound 6 as a white solid.

Found C 59.0%, H 5.5%, N 5.5%, P 6.1%; $C_{24}H_{27}N_2O_7P$ requires C 59.25%, H 5.6%, N 5.75%, P6.35%.

NMR characterisation as a 1:1 mixture of diastereoisomers at phosphorus:

$^{31}P$ nmr $^1H$ decoupled ($CDCl_3$, 162 MHz) δ37.6, 37.2 ppm.

Example 7

The example describes the preparation of the compound of formula

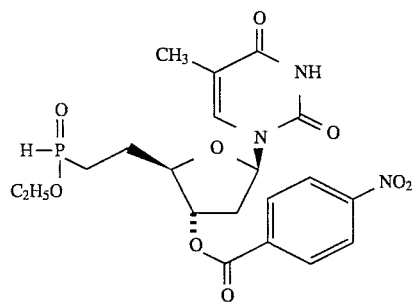

Compound 7

Trimethylsilylchloride (14 ml, 0.11 mmole) is added dropwise (2 minutes) to a stirred solution of Compound 4 (7 g, 11.7 mmole) and ethanol (1 ml) in chloroform (150 ml) under argon. The resulting solution is allowed to stand at room temperature overnight and then concentrated in vacuo to give a pale yellow foam which is purified by flash silica column chromatography (gradient elution: chloroform/ethanol 40:1→20:1) to give Compound 7 as a white solid.

Found C 49.4%, H 5.1%, N 8.4%, P 6.3%; $C_{20}H_{24}N_3O_9P.⅓H_2O$ requires C 49.3%,H 5.1%, N 8.6%, P 6.35%.

NMR characterisation as a 1:1 mixture of diastereoisomers at phosphorus:

$^{31}P$ nmr $^1H$ decoupled (36.4 MHz), $CDCl_3$) δ36.3, 35.9 ppm.

Example 8

This Example describes the preparation of

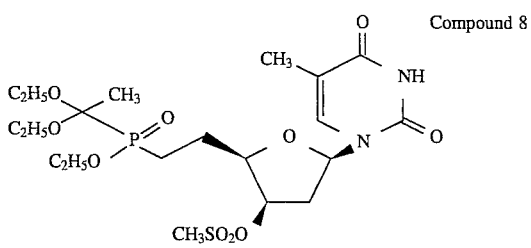

Compound 8

To a mixture of Compound 1 (2 g, 4.46 mmole) and dimethylaminopyridine (50 mg) in pyridine (10 ml), under argon, is added methane sulphonyl chloride (1.5 ml, 19.4 mmole) with stirring. The resulting mixture is allowed to stand at ambient temperature overnight and then concentrated under high vacuum. The resulting brown solid is purified by flash silica column chromatography (chloroform-ethanol, gradient elution 50:1–10:1) and then by further flash silica column chromatography (chloroform-ethanol 25:1) to give Compound 8 as an off-white foam.

$^{31}P$ n.m.r. $^1H$ decoupled ($CDCl_3$, 36.4 MHz) δ47.9 ppm.

example 9

This Example describes the preparation of

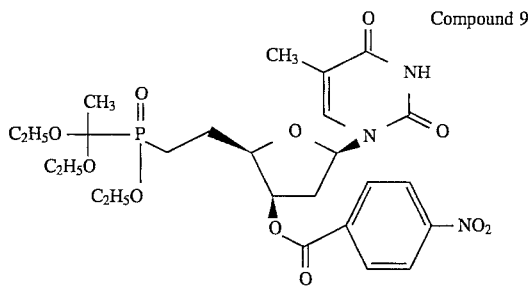

Compound 9

A mixture of Compound 1 (500 mg, 1.1 mmole) and 4-nitrobenzoic acid chloride (250 mg, 1.35 mmole) in pyridine (5 ml) under an atmosphere of argon is stirred for 24 hours. The resulting suspension is concentrated in vacuo and purified by flash silica column chromatography (chloroform-ethanol, 50:1) to give Compound 9 as a white solid.

Found: C 51.9, H 6.2, N 6.8, P 4.9%;

Required for $C_{26}H_{36}N_3O_{11}P$: C 52.25, H 6.05, N 7.05, P 5.2%.

$^{31}P$ n.m.r. $^1H$ decoupled ($CDCl_3$ 36.4 MHz) δ47.6, 47.4 ppm.

Example 10

This Example describes the preparation of

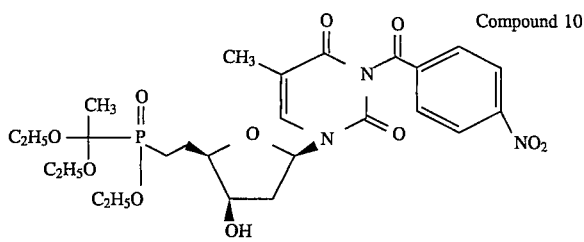
Compound 10

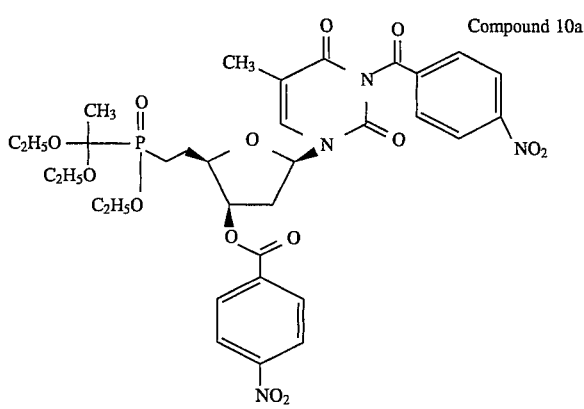
Compound 10a

To a solution of Compound 1 (500 mg, 1.1 mmole) and triethylamine (0.19 ml, 1.34 mmole) in dry dichloromethane (5 ml) under argon is slowly added, at 0° C., a solution 4-nitrobenzoic acid chloride (250 mg, 1.35 mmole) dissolved in a mixture of dichloromethane (2 ml) and tetrahydrofuran (2 ml). After 1 minute, a yellow solution is formed and cooling is stopped. After 18 hours, concentration gives a yellow oily solid which is purified by flash silica column chromatography (chloroform-ethanol 40:1) to give compound 10a as the minor fraction together with compound 10 as the major fraction, m.pt 63°–6° C.

Found: C 52.1, H 6.1, N 6.8, P 5.3%; $C_{26}H_{36}N_3O_{11}P$ requires C 52.25, H 6.05, N 7.05, P 5.2%.

$^{31}P$ nmr $^1H$ decoupled (CDCl$_3$, 36.4 MHz) δ51.1, 50.8 ppm.

Example 11

This Example describes the preparation of the compound of formula

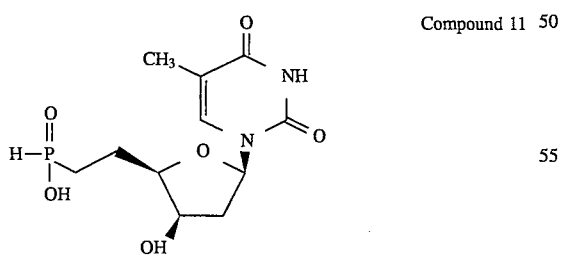
Compound 11

Trimethylsilyl chloride (28 ml, 22 mmole) is added dropwise at room temperature to a stirred solution of Compound 1 (1.0 g, 2.2 mmole) and ethanol (1 ml) in chloroform (20 ml) under argon. The resulting solution is allowed to stand at room temperature overnight and then concentrated in vacuo to give a crude solid. Purification by flash silica column chromatography (eluant 30:1 chloroform/ethanol) followed by methanol alone gives, on concentration of the methanol traction, the crude product (0.7 g). Further purification by passage through Dowex 50W×2 (50–100 mesh) (eluant water) and lyophyllisation gives Compound 11 as a white solid. $[\alpha]_D^{25}$–2.41°, c 1.03 methanol $^{31}P$ nmr $^1H$ decoupled (D$_2$O, 162 MHz) δ36.0 ppm.

$^1H$ nmr (CD$_3$OD, 400 MHz) δ7.88 (1H, m, H6), 7.08 (1H, dt, J$_{HP}$541 Hz, J$_{HH}$2 Hz, P$\underline{H}$), 6.13 (1H, dd, J8, 2 Hz, H-1$^1$), 4.25 (1H, dd, J5, 3 Hz, H3$^1$), 3.90 (1H, m, H4$^1$), 2.65 (1H, ddd, J15, 8, 5 Hz, H2$^1$), 2.14–1.84 (5H, m, C$\underline{H}_2$C$\underline{H}_2$P, H2$^1$), 1.88 (2H, d, J 1 Hz, CH$_3$) ppm Found C,41.3; H, 5.7, N, 8.7, P, 9.5%;

$C_{11}H_{17}N_2O_6P.H_2O$ requires C, 41.0; H, 5.95; N, 8.7; P, 9.6%.

$^{13}C$ nmr (CD$_3$OD; 100 MHz) δ166.4 (C4), 152.4 (C2), 139.2 (C6), 110.8 (C5), 85.7 (C1$^1$), 85.7 (d, J$_{cp}$ 16 Hz, C4$^1$), 70.55 (C3$^1$), 42.2 (C2$^1$), 27.4 (d, J$_{cp}$93 Hz, $\underline{C}$H$_2$P), 21.5 ($\underline{C}$H$_2$CH$_2$P), 12.45 (CH$_3$) ppm.

Example 12

This Example describes the preparation of the compound of formula

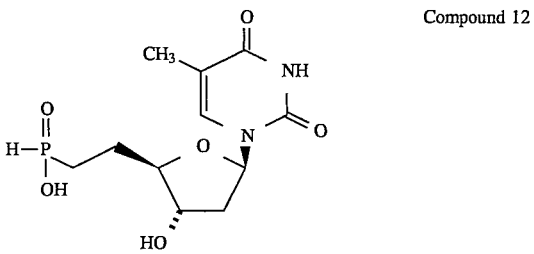
Compound 12

A mixture of Compound 7 (0.708, 1.6 mmole) and sodium hydroxide (0.168, 4 mmole) in methanol (20.6 ml) is stood at room temperature for 19 hours. The mixture is concentrated to yield a yellow solid which is dissolved in water (10 ml) and washed with dichloromethane (7×25 ml). Concentration of the aqueous layer gives crude product (0.88) which is purified by passage through Dowex 50W×2 (50–100 mesh) (eluant water). Appropriate fractions are evaporated and lyophyllised to afford Compound 12 as a white foam.

$[\alpha]_D^{25}$ +23.63,° C. 1.03. MeOH found C, 40.6; H, 5.6; N, 8.8%; $C_{11}H_{17}N_2O_6P.H_2O$ requires C. 41.0; H, 5.95; N, 8.7%

$^{31}P$ nmr $^1H$ decoupled (162 MHz, D$_2$O), δ35.7 ppm.

$^1H$ nmr (400 MHz, D$_2$O) δ7.39 (1H, m, H-6), 7.03 (1H, d, J$_{JP}$ 546 Hz, P$\underline{H}$) 6.19 (1H, t, J 7 Hz, H1$^1$), 4.29 (1H, dt, J 6.4 Hz, H3$^1$), 3.89 (1H, m, H4$^1$), 2.34 (1H, ddd, J14, 7 and 7 Hz, H2$^1$), 2.29 (1H, ddd, J14, 7 and 4 Hz, H2$^1$), 2.00–1.75 (4H, m, C$\underline{H}_2$C$\underline{H}_2$P), 1.84 (3H, d, J1 Hz, CH$_3$) ppm.

$^{13}C$ nmr (D$_2$O, 100 MHz), 169.15 (C4), 154.35 (C2), 140.05 (C6), 114.4 (C5), 88.75 (d, J$_{CP}$ 17 Hz, C4$^1$), 87.7 (C1$^1$), 75.95 (C3$^1$), 40.5 (C2$^1$), 28.5 (d, J$_{CP}$91 Hz, $\underline{C}$H$_2$P), 27.1 ($\underline{C}$H$_2$CH$_2$P), 14.3 (CH$_3$) ppm.

Example 13

This Example describes the preparation of the compound of formula

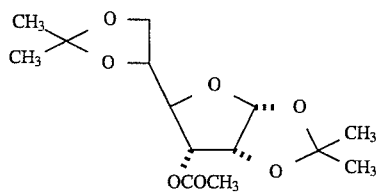

Compound 13

A mixture of 1,2,5,6-di-O-isopropylidene-α-D-allofuranose (the diacetonide of formula XV) prepared according to Carbohyd. Res. 24(1972) 192 (55.72 g., 0.214M), acetic anhydride (100 ml), and pyridine (50 ml) is stirred at room temperature for 3 hours. The solution is evaporated then co-evaporated with methanol three times to remove the excess of acetic anhydride and pyridine. The residue is dissolved in dichloromethane (200 ml), washed several times with water and dried (Mg SO$_4$). Evaporation gives a white solid, m.pt.75° C., $[\alpha]_D^{25}$ + 109.4,° C. 1.03 CHCl$_3$.

Found C 55.5, H 7.30; Calculated for $C_{14}H_{22}O_7$ C 55.6, H, 7.3%

Example 14

This Example describes the preparation of the compound of formula

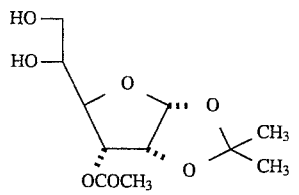

Compound 14

Compound 13 (65 g 0.215M) is dissolved in 80% acetic acid (250 ml) and allowed to stand for 60 hours. The acetic acid is removed by evaporation and co-evaporation with methanol to give a pale yellow oil. This oil is chromatographed on silica (750 g) using ethyl acetate eluant to give Compound 14 as a colourless oil. $[\alpha]_d^{20}$+125.2,° C. 1.15 CHCl$_3$ Found C 50.1, H 7.0; Calculated for $C_{11}H_{18}O_7$ C 50.4, H 6.9%

Example 15

This Example describes the preparation of the compound of formula

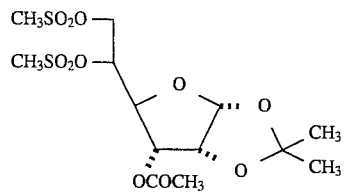

Compound 15

Compound 14 (45.9 g, 0.175M) in pyridine (180 ml) under argon is cooled to 5° C. and methanesulphonyl chloride (60.1 g, 0.525M) is added over 1 hour. The temperature is allowed to rise to room temperature and the mixture is stirred for a further 2.5 hours until the reaction, monitored by thin layer chromatography (TLC), appears complete. Chloroform (200 ml) and hydrochloric acid (2N, 300 ml), are added and the mixture is stirred for 5 minutes. The organic phase is separated, washed with sodium bicarbonate (250 ml) then brine (250 ml) and dried (MgSO$_4$). Evaporation of solvent gives a yellow oil (70 g) which is purified by flash chromatography using ether eluant to give Compound 15, m.pt. 84°–5° C., $[\alpha]_D^{25}$+109.6,° C. 0.75;

Found C 37.3, H 5.3; Calculated for $C_{13}H_{22}O_{11}S_2$, C 37.3, H 5.3%.

Example 16

This Example describes the preparation of the compound of formula

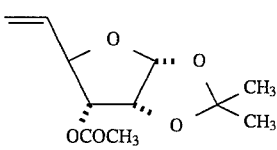

Compound 16

A mixture of Compound 15 (65 g, 0.155M) and sodium iodide (94 g, 0.62M) in butan-2-one (1.5l) is heated to reflux for 5 hours. A further 10% of sodium iodide is added and heating continued for 3 hours. The solvent is removed and the dark brown residue is partitioned between chloroform and water. Sodium thiosulphate is added portionwise until the solution is colourless. The chloroform extracts are separated, washed with sodium bicarbonate then brine and dried (MgSO$_4$). Evaporation gives a pale yellow oil which is purified by chromatography on silica using hexane: ethyl acetate, 2:1, eluant, to give Compound 16. An analytical sample is obtained by bulb to bulb distillation (100° C./0.1 mm Hg), $[\alpha]_D^{25}$+107.5, c 1.13 CHCl$_3$;

Found C 58.0, H 7.0; $C_{11}H_{16}O_5$ requires C 57.9, H 7.1%.

Example 7

This Example describes the preparation of the compound of formula

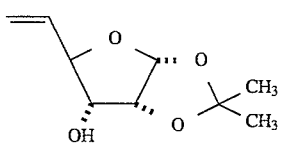

Compound 17

Compound 16 (15 g 0.066M) dissolved in methanol (100 ml) is added to a solution of potassium carbonate (22.7 g, 0.165M) in water (100 ml). After 15 minutes the reaction is complete (TLC).

The solvent volume is reduced to 50 ml and after further co-evaporation with water the residue is washed with chloroform (3×100 ml). The chloroform extracts are washed with brine then dried (MgSO$_4$). Evaporation gives a white solid, re.pt. 67.5°–68° C., $[\alpha]_D^{25}$+38.2,° C. 0.95 CHCl$_3$.

Found C 57.8, H 8.0; Calculated for $C_9H_{14}O_4$, C 58.05, H 7.6%.

Example 18

This Example describes the preparation of the compound of formula

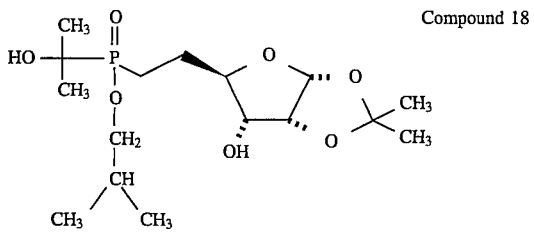

Compound 18

A solution of isobutyl (1-hydroxy-1-methylethyl) phosphinate (7.22 g, 0.0403M) and t-butylcyclohexylperdicarbonate (0.5 g) in toluene (1 ml) is heated to 80° C. and stirred under argon. A solution of Compound 17 and t-butyl cyclohexylperdicarbonate (2 g) in toluene (4 ml) is added slowly over 30 minutes and the mixture is stirred for 4 hours. When reaction is complete (monitored by $^{31}$P nmr) the solvent is evaporated in vacuo to give a pale yellow oil. The oil is chromatographed on silica using ether, ethyl acetate and finally 5% methanol in ethyl acetate gradient as eluants. There is obtained Compound 18 as an oil which partly solidifies.

Found C 52.7, H 8.5, P 8.7; $C_{16}H_{30}O_7P$ requires C 52.6, H 8.3 P 8.5%.

$^{31}$P nmr (CDCl$_3$, 162 MHz): δ56.85, 57.2 ppm.

Example 19

This Example describes the preparation of the compound of formula

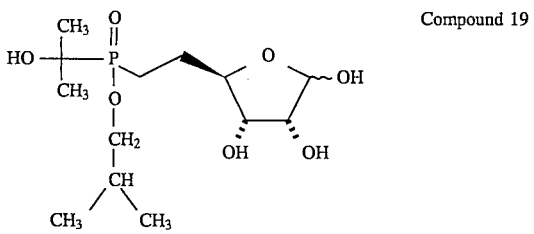

Compound 19

To Compound 18 (8.25 g, 0.0226M) in dimethoxyethane (200 ml) is added a slurry (50 ml) of Dowex 50W×2 (100), H$^+$ form, in water and the mixture is heated to 80° C. for 12 hours then cooled. The Dowex is removed by filtration to give a pale yellow solution. Evaporation of the solvent gives Compound 19 as an oil which is not purified further.

$^{31}$P nmr (CD$_3$OD, 162 MHz): δ=63.2, 63.4, 64.3 and 64.4 ppm.

Example 20

This Example describes the preparation of the compound of formula

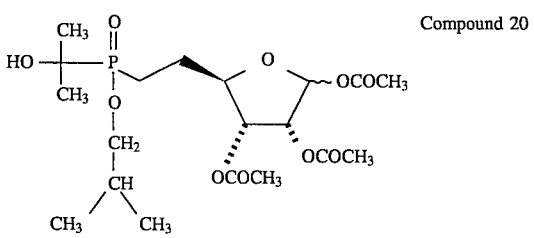

Compound 20

Compound 19 (20 g, 0.0613M) is added to a mixture of pyridine (40 ml) and acetic anhydride (40 ml) with cooling, maintaining the temperature below 30° C. Reaction is complete in 20 minutes (Monitored by TLC). The excess of acetic anhydride and pyridine are removed by evaporation. The residual oil is dissolved in chloroform and washed with dilute hydrochloric acid, sodium bicarbonate and brine and dried over MgSO$_4$. Evaporation gives a yellow syrup which is purified by chromatography with silica. There is obtained Compound 20. Found C 50.4; H 7.15, P 6.65; $C_{19}H_{32}O_{10}P$ requires C 50.55, H 7.15, P 6.9%.

$^{31}$P nmr (CDCl$_3$, 162 MHz): δ55.5, 55.7, 55.8 ppm.

Example 21

This Example describes the preparation of the compound of formula

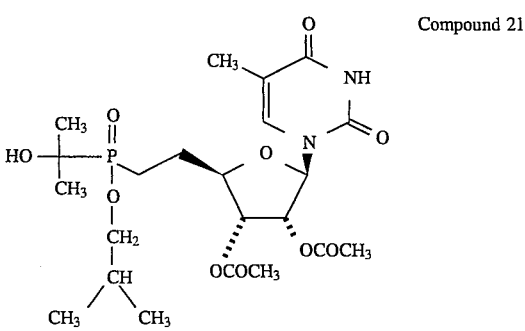

Compound 21

A mixture of thymine (6.31 g, 0.05M), N, O-bis trimethylsilyl acetamide (20.34 g, 0.1M) and dichloroethane (125 ml) is heated to 80° C. under argon until a clear solution is obtained. The solution is cooled to room temperature and a solution of Compound 20 (22.57 g, 0.05M) in dichloroethane (75 ml) is added followed by trimethylsilyltrifluoromethane sulphonate (32.91 g, 0.125M). The reaction mixture is heated to 50° C. and stirred for 8 hours until reaction is complete (TLC). Chloroform (300 ml) and water (200 ml) are added followed by saturated sodium bicarbonate solution until the aqueous phase is neutral. The mixture is washed with chloroform (3×100 ml) and the extracts are washed with water then brine and dried (MgSO$_4$). Evaporation gives a viscous liquid which is chromatographed on silica using 5% methanol in chloroform as eluant. There is obtained a colourless oil which is dissolved in acetic acid, water and tetrahydrofuran (100 ml 3:1:1 ratio) and heated on a steam bath for 15 minutes. The solvent is removed by evaporation followed by co-evaporation with methanol then chloroform. There is obtained Compound 21 as a white hygroscopic solid.

Found C 50.9, H 6.9, N 5.2, P 5.9; $C_{22}H_{35}O_{10}N_2P$ requires C 50.95, H 6.8, N 5.4, P 5.0%.

$^{31}$P nmr (CDCl$_3$, 162 MHz): δ56.0, 56.3 ppm.

Example 22

This Example describes the preparation of the compound of formula

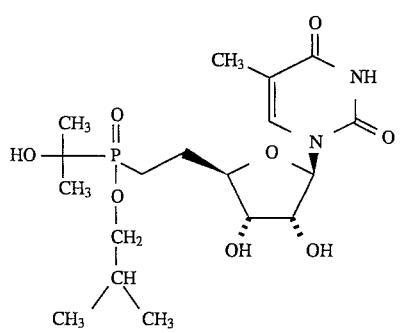

Compound 22

Compound 21 (4.4 g, 0.0085M) dissolved in methanol (5 ml) is added to potassium carbonate (2.34 g, 0.017M) in water (5 ml) and the mixture is stirred for 15 minutes. The mixture is evaporated to dryness and the residue is stirred with acetone. The inorganic solids are removed by filtration and the acetone is evaporated to give Compound 22 as an oil.

$^{31}$P nmr (D$_2$O, 162 MHz): δ=63.0 ppm.

Example 23

This Example describes the preparation of a compound of formula

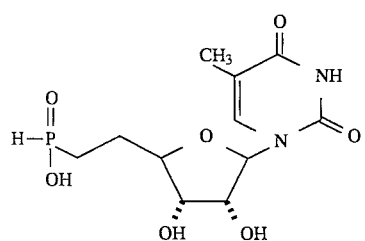

Compound 23

Compound 22 (3.7 g) is dissolved in 10% aqueous ammonia and heated up to 80° C. for 12 hours. The mixture is cooled and evaporated to an oil which is purified on ion exchange resin Dowex 50W X 2 (100) acid form using water as eluant. There is obtained Compound 23 as a white foamy solid which is lyophilised to a white hygroscopic solid.

Found: C 40.9, H 5.3, N 8.3, P 9.4%; C$_{11}$H$_{17}$N$_2$O$_7$P requires C 41.25, H 5.35, N 8.75, P 9.7%.

$^{31}$P nmr (D$_2$O, 162 MHz):δ36.3 ppm, J$_{PH}$=540 Hz.

Example 24

This Example describes the preparation of the compound of formula

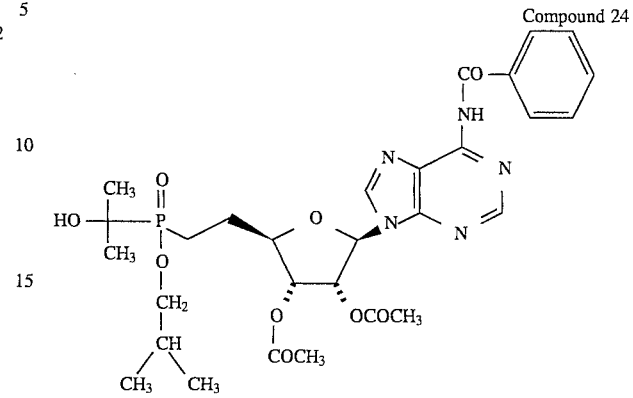

Compound 24

Benzoyladenine (0.795 g, 0.0033M), N,O-bis trimethylsilylacetamide (1.35 g, 0.0066M) and dichloroethane (5 ml) are heated to 80° C. under argon for 15 minutes to give a clear solution. The mixture is cooled to room temperature and Compound 20 (1.5 g, 0.0033M) in dichloroethane (5 ml) is added followed by trimethylsilyltrifluoromethane sulphonate (2.22 g, 0.0099M). The mixture is heated to 50° C. for 13 hours. Chloroform (50 ml) is added and then sodium bicarbonate solution until the pH reaches 7. The chloroform extracts are washed with brine and dried (MgSO$_4$). Evaporation gives a yellow solid which is purified by chromatography on silica using 2% methanol in chloroform as eluant. There is obtained a colourless oil which is heated with acetic acid/tetrahydrofuran/water (20 ml, 3:1:1 ratio) at 60° C. for 3 hours.

Evaporation of the resulting mixture gives an oil which is chromatographed on silica using 5% methanol in chloroform as eluant. There is obtained Compound 24 as a dihydrate.

Found: C 52.1, H 5.9, N 10.6%, C$_{29}$H$_{38}$N$_5$O$_9$P.2H$_2$O requires C 52.1, H 6.3, N 10.5%

$^{31}$P nmr (CDCl$_3$, 162 MHz):δ56.0 ppm.

Example 25

This Example describes the preparation of a compound of formula

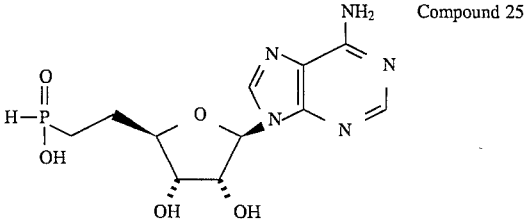

Compound 25

Compound 24 (0.55 g, 0.00087M) and potassium carbonate 0.12 g, 0.0087M) are dissolved in methanol (2 ml) and water (2 ml) and stirred for 15 minutes. The solution is evaporated to dryness and aqueous ammonia (i0%, 20 ml) is added. The solution is stirred at 80° C. for 6 hours then evaporated to an oil. The oil is dissolved in water (2 ml) and neutralised with acetic acid. The solution is passed down an ion exchange resin, Dowex 50W X 2 (100), eluting first with water and then with 1% aqueous ammonia. The ammonia eluates are evaporated and co-evaporated with water then methanol to give Compound 25.

$^{31}$P NMR (D$_2$O, 162 MHz) δ=29.9 ppm, J$_{PH}$=505 Hz.

Example 26

This Example describes the preparation of a compound of formula

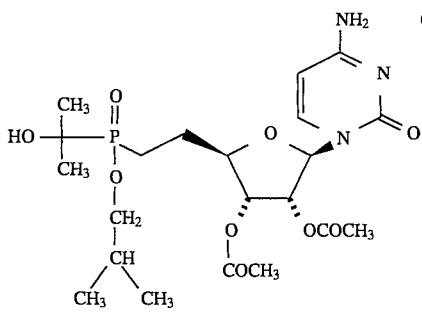

Compound 26

A mixture of cytosine (0.111 g, 0.001M), N,O-bistrimethylsilylacetamide (0.814 g, 0.004M) and dichloroethane (2.5 ml) is heated to 80° C. under argon for 30 minutes to give a clear solution. The mixture is cooled to room temperature and Compound 20 (0.45 g, 0.001M) in dichloroethane (2.5 ml) and trimethylsilyltrifluoromethanesulphonate (0.667 g, 0.003M) are added. The reaction mixture is warmed to 70° C. for 3 hours. Chloroform (20 ml) and water (5 ml) are added, followed by saturated sodium bicarbonate solution until the pH is 7. The mixture is washed with chloroform (2×10 ml), and the organic extracts are washed with brine, dried (MgSO$_4$) and evaporated to give an oil which is chromatographed on silica using 10% methanol in chloroform. There is obtained a colourless oil which is dissolved in acetic acid, water and tetrahydrofuran (5 ml, 3:1:1 ratio) and heated on a steam bath for 15 minutes. The solvent is removed by evaporation followed by co-evaporation with methanol and chloroform. There is obtained Compound 26 as a white hygroscopic solid.

$^{31}$P nmr (CDCl$_3$, 162 MHz):δ56.9, 57.1 ppm.

Example 27

This Example describes the preparation of a compound of formula

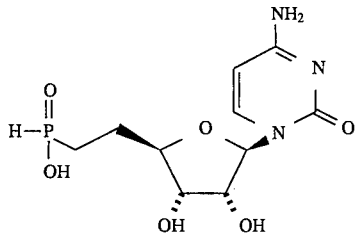

Compound 27

A mixture of Compound 26 (0.18 g, 0.00036M) and potassium carbonate (0.15 g, 0.001M) is dissolved in methanol (2 ml) and water (2 ml) and stirred for 1 hour. The solution is evaporated to dryness and the residual solid is dissolved in 10% aqueous ammonia (10 ml) and heated at 80° C. for 2 hours. The solution is evaporated and passed down an ion exchange column of Dowex 50W X 2 (100), eluting with water then 1% ammonia solution. There is obtained an oil which is lyophilised to give Compound 27 as a white solid.

$^{31}$P nmr (D$_2$O, 162 MHz) δ=30 ppm, J$_{PH}$=505 Hz.

Example 28

This Example describes the preparation of a compound of formula

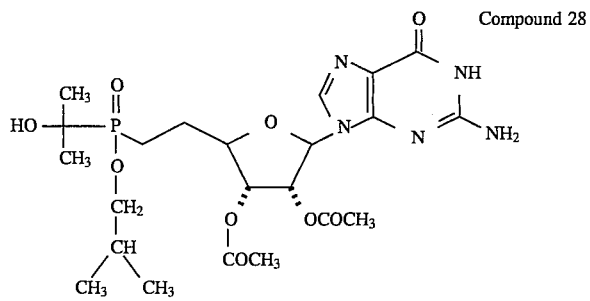

Compound 28

A mixture of guanine (0.15 g, 0.001M), N,O-bistrimethylsilylacetamide (1.01 g, 0.005M) and dichloroethane (2.5 ml) is heated to 80° C. for 3 hours under argon. The resulting clear solution is cooled to room temperature and Compound 20 (0.45 g, 0.001M) in dichloroethane (2.5 ml) and trimethylsilyltrifluoromethanesulphonate (0.666 g, 0.003M) are added. The mixture is heated for 5 hours at 50° C. Chloroform (I 0 ml) is added, followed by saturated sodium bicarbonate until the pH is 7. The mixture is washed with chloroform (2×10 ml) and the organic extracts are washed with brine, dried (MgSO$_4$) and evaporated to give a yellow syrup (0.5 g). This oil is dissolved in acetic acid, water and tetrahydrofuran (5 ml 3:1:1 ratio) and heated for 15 minutes. The solvent is removed by evaporation and co-evaporation with methanol and chloroform. There is obtained compound 28 as an oil which is purified by chromatography on silica using 10% methanol in chloroform as eluant.

$^{31}$P NMR (CDCl$_3$, 162 MHz) δ=56.7, 57.3 ppm.

Example 29

This Example describes the preparation of compounds of formulae

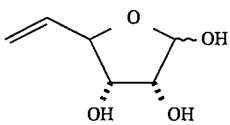

Compound 29

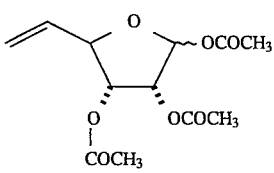

Compound 30

To Compound 17 (11 g, 0.059M) is added a slurry (25 ml) of Dowex (50W X 2 acid form) in water and the mixture is stirred at 70° C. for 5 hours. The mixture is cooled and the resin is filtered off. The aqueous filtrate is evaporated to dryness to give Compound 29 Which is used in the subsequent step without further purification. Compound 29 (8.5 g, 0.058M), acetic anhydride (50 ml) and pyridine (50 ml) are allowed to stand at room temperature for 2 hours. The reaction mixture is poured on to ice and concentrated hydrochloric acid is added. The mixture is washed with ethyl acetate and the organic solution washed with saturated sodium bicarbonate then water and dried ($MgSO_4$). Evaporation of the solvent gives Compound 30 as a mixture of α- and β-anomers. The product is purified by chromatography on silica using hexane/ethylacetate (5:1) as eluant. There is obtained successively the β-anomer, a mixture of α- and β-anomers and finally the α-anomer.

Found: C 52.6, H 5.9%

$C_{21}H_{16}O_7$ requires C 52.9, H 5.9%

Example 30

This Example describes the preparation of a compound of formula

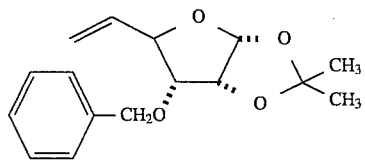

Compound 31

Sodium hydride (4.0 g, 0.1 M, 60% dispersion in oil) is rinsed with petroleum ether (40°–60° C.) and added to tetrahydrofuran (75 ml) under argon. The mixture is cooled to −10° C. and Compound 17 (18.62 g, 0.1M) in tetrahydrofuran (50 ml) is added dropwise maintaining the temperature at −5° C. The solution is warmed to 5° C. and benzyl bromide (11.9 ml, 0.1M) and tetra-n-butylmmmonium iodide (0.37 g, 0.001M) in tetrahydrofuran (25 ml) are added slowly. The mixture is allowed to warm to room temperature and stirred for a further three hours when reaction is complete (monitored by T.L.C. in ether). Horisil (5 g) is added and the solvent is evaporated. The residue is mobilised with hexane (50 ml) and the solids are filtered off. The filtrate is evaporated to a yellow oil which is purified by 'bulb to bulb' distillation (150° C., 1 mm Hg) to give 26.9 g oil. This oil is chromatographed on silica using 10% ethyl acetate in petroleum ether (40°–60° ) to give Compound 31.

Found: C 69.6, H 7.5%; calculated for $C_{16}H_{20}O_4$, C 69.5, H 7.2%.

Example 31

This Example describes the preparation of

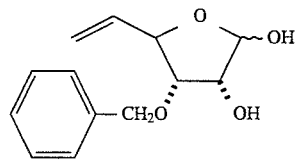

Compound 32

Compound 31 (10.0 g, 0.036M) is added to a slurry (40 ml) of Dowex (50W X 2, acid form) and dimethoxyethane (125 ml) and the mixture is heated to 80° C. for 8 hours. The Dowex is removed by filtration and the solvent is evaporated. The residual oil is purified by flash chromatography using silica and hexane/ethyl acetate (1:1) as eluant. There is obtained Compound 32, which is used directly in the preparation of Compound 33.

Example 32

This Example describes the preparation of

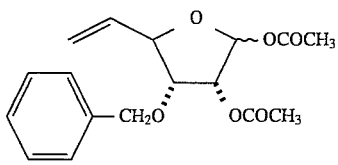

Compound 33

A mixture of Compound 32 (4.6 g, 0.0195M), acetic anhydride (7.5 ml), and pyridine (15 ml) is stirred at room temperature for 3 hours. Iced water (50 ml) is added and the solution is washed with ether (2×50 ml). The ether is separated, washed with dilute hydrochloric acid (50 ml), saturated sodium bicarbonate (50 ml) and brine (50 ml) and then dried ($MgSO_4$). Evaporation of the solvent gives a yellow oil which is purified by chromatography on silica using hexane/ethyl acetate (3:1) as eluant. Them is obtained Compound 33 as a mixture of α- and β-anomers.

Found: C 63.9, H 6.2%; $C_{17}H_{20}O_6$ requires C 63.7, H 6.3%

Example 23

This Example describes the preparation of

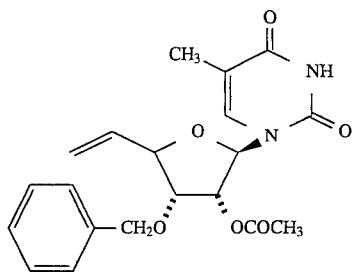

Compound 34

A mixture of thymine (0.197 g, 0.00156M) and bistrimethylsilylacetamide (0.63 g, 0.0031M) in dichloroethane (5 ml) is heated for 1 hour at 80° C. under argon. The clear solution obtained is cooled and Compound 33 (0.5 g, 0.00156M) in dichloroethane (10 ml) followed by trimethylsilyltrifluoromethanesulphonate (0.59 g, 0.0023M) are added. The mixture is heated at 75° C. for 3 hours. After cooling the mixture, chloroform (10 ml) is added, followed by sodium bicarbonate until the pH is neutral. The organic phase is separated, washed (water) and dried ($MgSO_4$). Evaporation of the solvent gives a yellow syrup (0.6 g) which is purified by chromatography on silica using hexane/ethyl acetate (1:1) as eluant. There is obtained Compound 34 as a white hygroscopic solid.

Found: C 61.9, H 6.0, N 7.2%; $C_{20}H_{22}N_2O_4$ requires C 62.2, H 5.7, N 7.2%.

Example 34

This Example describes the preparation of

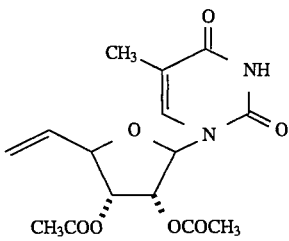

Compound 35

A mixture of thymine (0.505 g, 0.004M), bistrimethylsilylacetamide (1.624 g, 0.008M) and dichloroethane (10 ml) is heated for 1 hour at 80° C. under argon. The resulting clear solution is cooled to room temperature and Compound 30 (1.088 g, 0.004M) in dichloroethane (10 ml) followed by trimethylsilyltrifluoromethane sulphonate (1.332 g, 0.006M) are added. The mixture is heated for 3 hours at 70° C. After cooling the mixture, chloroform is added, followed by sodium bicarbonate until the pH is neutral. The organic phase is separated, washed (water) and dried (MgSO$_4$). Evaporation of the solvent affords a yellow oil which is purified by chromatography on silica using hexane/ethyl acetate (1:1) as eluant. There is obtained Compound 35 as a white hygroscopic solid, which is used directly in the preparation of Compound 36.

Example 35

This Example describes the preparation of

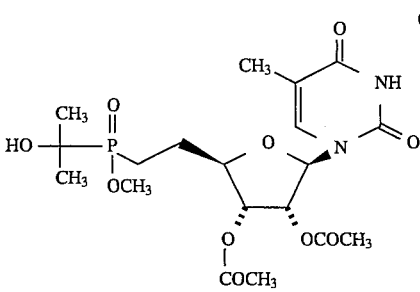

Compound 36

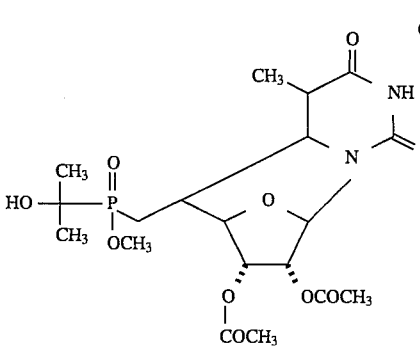

Compound 37
(By-product)

Methyl(1-hydroxy-1-methylethyl)phosphinate (0.82 g, 0.006M) and t-butylcyclohexylperdicarbonate (0.25 g) as initiator are heated to 70° C. under argon with stirring. Compound 35 (0.92 g, 0.003M) is added portionwise over 3 hours together with more initiator [3×0.05 g in toluene (0.25 ml)]. The mixture is stirred for a further 4 hours at 80° C., cooled, then partitioned between ethyl acetate and water. The aqueous phase is evaporated and the excess of phosphinate removed by distillation (100° C./0. 1 mm). The residual solid is purified by chromatography on silica using 10% ethanol in ethyl acetate as eluant. There is obtained Compound 36 and a by-product Compound 37.

$^{31}$P NMR (CDCl$_3$, 162 MHz)

δ=57.7, 56.9, 56.6 ppm. (cpd 36)

δ=56.0, 56.5, 56.6, 56.8 ppm (cpd 37)

Example 36

This Example describes the preparation of

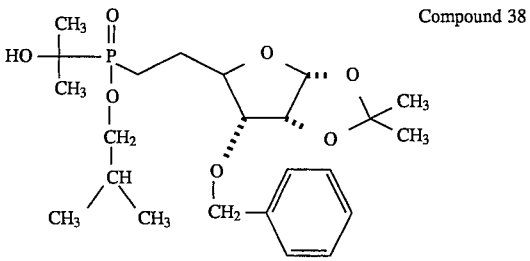

Compound 38

A solution of isobutyl(1-hydroxy-1-methylethyl)phosphinate (12.6 g, 0.07M) and tert-butylcyclohexylperdicarbonate (0.5 g) in toluene (2 ml) is heated at 80° C. under argon. Compound 31 (19.34 g, 0.07M) in toluene (2 ml) is added portionwise over 2 hours. A further 2.5 g perdicarbonate in toluene (6 ml) is added over 2 hours. The reaction mixture is stirred for a further 10 hours, adding perdicarbonate (0.25 g) every 2 hours when the reaction appears complete ($^{31}$P nmr). The mixture is cooled and evaporated to a gum which is purified on silica by flash chromatography using ethyl acetate, then 5% methanol in ethyl acetate, as eluants. The methanolic eluates were re-chromatographed on silica using 5% methanol in ethyl acetate as eluant to give Compound 38.

$^{31}$P nmr (CDCl$_3$ 162 MHz) δ=56.0, 56.2 ppm.

Example 37

This Example describes the preparation of

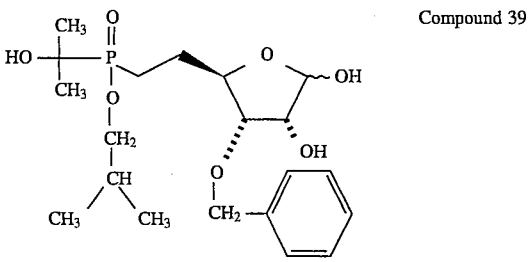

Compound 39

Compound 38 (15.07 g, 0.033M), tetrahydrofuran (150 ml) and dilute hydrochloric acid (150 ml, 1M) are stirred at room temperature for 24 hours, then at 40° C. for 8 hours. The resulting solution is neutralised with solid sodium bicarbonate and then evaporated. The residue is dissolved in water and washed with ethyl acetate (3×50 ml). The organic extracts are washed with brine and dried (MgSO$_4$). Evaporation of the solvent gives Compound 39, which is further purified by chromatography on silica using 5% methanol in ethyl acetate.

Found: C 57.5, H 8.4%;

C$_{20}$H$_{33}$O$_7$P requires C 57.68, H 7.99%

$^{31}$P nmr (CDCl$_3$ 162 MHz) δ=56.7, 56.9, 57.3, 57.8 ppm

Example 38

This Example describes the preparation of

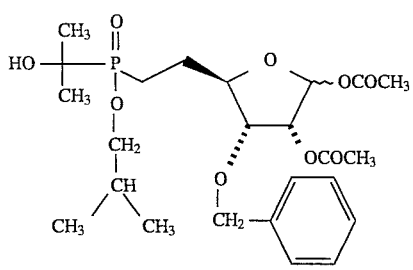

Compound 40

Compound 39 (10.41 g, 0.025M) and acetic anhydride (100 ml) in pyridine (100 ml) are allowed to stand at room temperature for 18 hours. The solution is evaporated to dryness and the residue is dissolved in chloroform (100 ml), washed successively with dilute hydrochloric acid (100 ml), sodium bicarbonate (100 ml), brine (100 ml) and then finally dried (MgSO$_4$). Evaporation gives Compound 40, which is used directly in the preparation of Compound 41.

$^{31}$P nmr (CDCl$_3$, 162 MHz) δ=55.5, 55.7, 55.9 ppm.

Example 39

This Example describes the preparation of

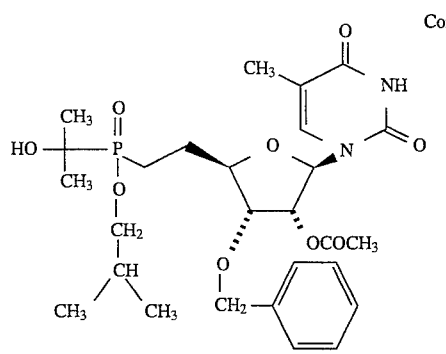

Compound 41

A mixture of thymine (2.02 g, 0.004M) N, O-bistrimethylsilylacetamide (1.63 g, 0.008M) and dichloroethane (10 ml) is heated at 80° C. under argon for 2 hours to give a colourless solution. The solution is cooled to room temperature and a solution of Compound 40 (2.02 g, 0.004M) in dichloroethane (15 ml) is added followed by trimethylsilyltrifluoromethane sulphonate (2.67 g, 0.012M). The mixture is heated at 50° C. for 3 hours. The resulting yellow solution is cooled and added to water (20 ml). Sodium bicarbonate is added until the pH is neutral. The aqueous phase is extracted with dichloromethane (3×10 ml) and the organic extracts are washed with brine and then dried (MgSO$_4$). Evaporation gives a white solid which is purified by chromatography using silica and a gradient of 2–5% methanol in ethyl acetate as eluant. There is obtained Compound 41 as a white hygroscopic solid.

$^{31}$P nmr (CDCl$_3$ 162 MHz) δ=56.3 ppm.

Example 40

This Example describes the preparation of

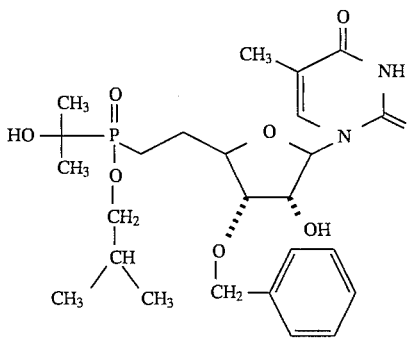

Compound 41

A mixture of Compound 41 (1.80 g, 0.0032M), potassium carbonate (0.438 g, 0.0032M), methanol (8 ml) and water (2 ml) is allowed to stand at room temperature for 15 hours. Evaporation gives a gum which is partitioned between water and ethyl acetate (10 ml). Extraction with ethyl acetate (3×10 ml) followed by a brine wash, drying (MgSO$_4$) and evaporation gives Compound 42 as a white solid.

$^{31}$P nmr (CDCl$_3$, 162 MHz) δ=56.3, 56.4 ppm.

Example 41

This Example describes the preparation of

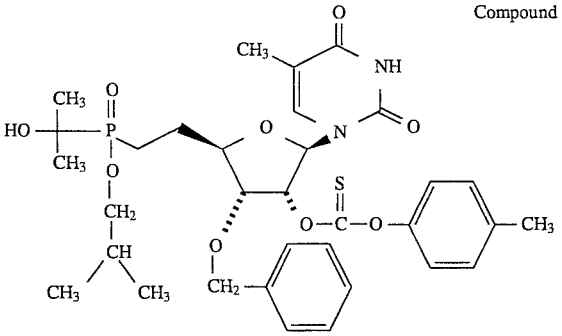

Compound 43

A mixture of Compound 42 (0.105 g, 0.0002M), p-tolylchlorothionoformate (0.041 g, 0.00022M), triethylamine (0.02 g, 0.0002M), dimethylaminopyridine (0.0048 g, 0.00004M) in dichloromethane (5 ml) is stirred at room temperature for 24 hours until reaction is complete by TLC. Dichloromethane (10 ml) is added and the solution is washed with sodium bicarbonate (10 ml), water and brine, then dried (MgSO$_4$). Evaporation of solvent gives an oil which is purified by chromatography using silica and 5% methanol in chloroform as eluant. There is obtained Compound 43.

$^{31}$P nmr (CDCl$_3$, 162 MHz) δ=56.33 ppm.

Example 42

This Example describes the preparation of

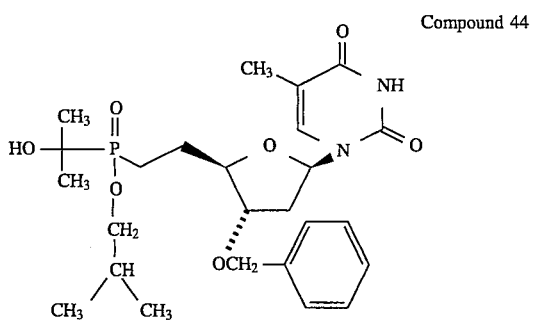

Compound 44

A mixture of Compound 43 (0.08 g, 0.1185 mM), tri-n-butylfinhydride (0.04 g, 0.142 mM), and A.I.B.N. (0.001 g) is heated to 100° C. in toluene (0.8 ml) for 4 hours. The reaction mixture is cooled and the toluene is removed by evaporation. The residue is dissolved in acetonitrile (2 ml) and washed with hexane (5×1 ml). The acetonitrile phase is separated and evaporated to give Compound 44, which is further purified by chromatography on silica using 2% methanol in chloroform as eluant.

$^{31}$P nmr (CDCl$_3$, 162 MHz) δ=62.9 ppm.

Example 43

This Example describes the preparation of

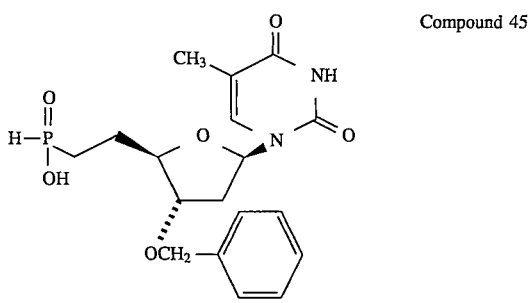

Compound 45

Compound 44 (13 mg, 0.025 mM), and aqueous ammonia (10%, 1 ml) are heated at 80° C. for 10 hours, then concentrated under vacuum on a rotary, evaporator. The residue is passed down Dowex (50W X 2) ion exchange resin to give Compound 45.

$^{31}$P nmr (CD$_3$OD, 162 MHz) δ=30.6 ppm, J$_{PH}$=505 Hz.

Example 44

This Example describes the preparation of

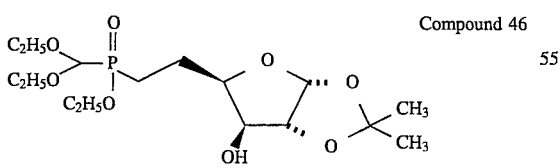

Compound 46

A compound of formula

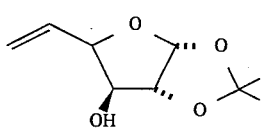

prepared as described by Hall, Hough and Pritchard, J. Chem. Soc. 1961, 1541 (0.56 g, 0.003M), ethyl(diethoxymethyl) phosphinate (0.59 g, 0.003M) and tertiarybutylcyclohexylperdicarbonate (0.1 g) are heated at 80° C. for 5 hours. The mixture is cooled and chromatographed on silica using a gradient of ether and 10% methanol in ether.

There is obtained Compound 46.

$^{31}$P nmr (CDCl$_3$ 36.4 MHz) δ=47.2 ppm.

Example 5

This Example describes the preparation of

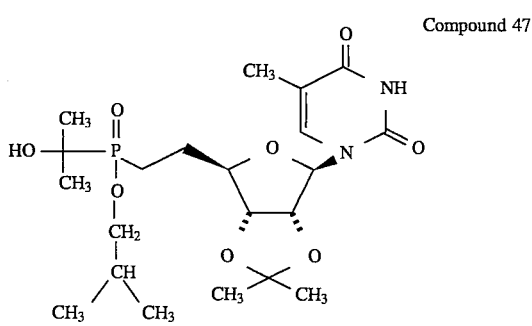

Compound 47

A mixture of Compound 22 (2.0 g, 0.0046M) 2,2-dimethoxypropane (20 ml), dimethylformamide (20 ml) and p-toluene sulphonic acid (0.1 g), is heated at 100° C. for 2.5 hours. The solution is concentrated to 10 ml, water (50 ml) is added and the product is extracted with ethyl acetate (3×50 ml). Concentration of the ethyl acetate phase gives an oil which is chromatographed on silica using 4% methanol in chloroform. There is obtained Compound 47.

$^{31}$P nmr (CDCl$_3$, 162 MHz) δ=56.05 ppm, 56.19 ppm.

Example 46

This Example describes the preparation of

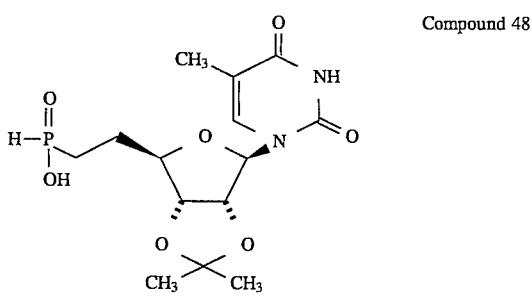

Compound 48

Compound 47 (1.71 g, 0.0036M) is heated in aqueous ammonia (10%, 20 ml) at 80° C. for 4 hours. Evaporation gives an oil which is stirred in methanol (10 ml) with Dowex 50W X 2 (2 g). Filtration and evaporation of the solvent gives Compound 48.

$^{31}$P nmr (CD$_3$OD, 162 MHz) δ=37.35 ppm, J$_{PH}$=540 Hz.

Example 47

This Example describes the preparation of

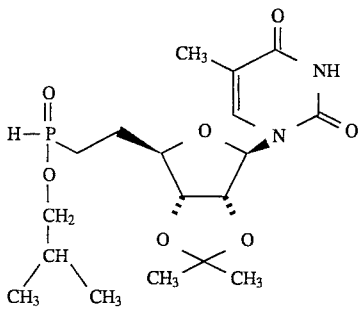

Compound 49

Compound 48 (0.8 g, 0.0022M), 2-methylpropanol (0.25 ml, 0.0026M), dimethylaminopyridine (0.1 g) in tetrahydrofuran (10 ml) are stirred at room temperature. Dicyclohexylcarbodiimide (0.55 g, 0.0026M) is added and stirring is continued for 3 hours. The precipitate is filtered off and the filtrate is evaporated in vacuo to give an oil which is chromatographed on silica using ethyl acetate then a gradient of 5% methanol in ethyl acetate. There is obtained Compound 49.

$^{31}$P nmr (CDCl$_3$ 162 MHz) δ=39.2 ppm, $J_{PH}$=540 Hz.

Example 48

This Example describes the preparation of

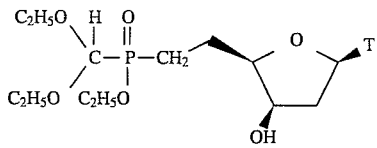

Compound 50 where T is 1-thyminyl.

To a solution of ethylmethyl(diethoxymethyl)phosphinate (1 ml, 5 mmole) in THF (10 ml), at −78° C. under an atmosphere of argon, is added n- butyllithium (3.1 ml, 1.6 molar solution in hexanes) dropwise over 20 minutes. The resulting solution is stirred at −78° C. for 1½ hours before addition of boron trifluoride etherate (0.615 ml, 5 mmole), followed after 5 minutes by the dropwise addition of a solution of 1-(3,5-anhydro-β-D-threo-pentafuranosyl)thymine (224 mg, 1 mmole) in THF (10 ml). The resulting solution is stirred for 1½ hours at −78° C. before the addition of a saturated solution of NaHCO$_3$ (3 ml). The resulting mixture is allowed to warm to room temperature over a few hours and then concentrated in vacuo. The resulting oil is passed through a short plug of silica with chloroform-ethanol (10:1) and concentrated to give a clear oil. Purification by flash silica column chromatography (chloroform-ethanol 15:1) gives Compound 50 as a hygroscopic white solid, isolated as a 1:1 mixture of diastereoisomers.

Found: C 49.8%, H 7.0%, N 6.3%, P 7.2%; C$_{18}$H$_{31}$N$_2$O$_8$P requires C 49.75%, H 7.2%, N 6.45%, P 7.15%.

$^{31}$P NMR $^1$H decoupled (CDCl$_3$, 36.4 MHz) δ47.5, 47.4 ppm.

Example 49

This Example describes the preparation of

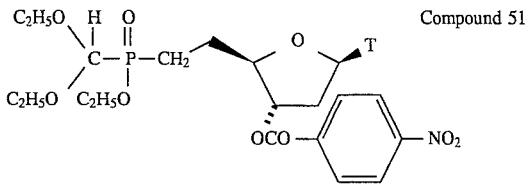

Compound 51 where T is 1-thyminyl.

Diethylazodicarboxylate (431.11, 0.27 mmole) is added dropwise to a solution of Compound 50 (100 mg, 0.23 mmole), triphenylphosphine (72 mg, 0.27 mmole) and p-nitrobenzoic acid (46 mg, 0.28 mmole) in a mixture of toluene (4 ml) and tetrahydrofuran (0.5 ml) under argon. After 19 hours, concentration and purification by flash silica column chromatography (chloroform-ethanol 40:1) gives Compound 51 as a viscous oil, isolated as a 1:1 mixture of diastereoisomers.

$^{31}$P nmr (CDCl$_3$, 161.9 MHz) δ45.9 ppm.

Example 50

This Example describes the preparation of

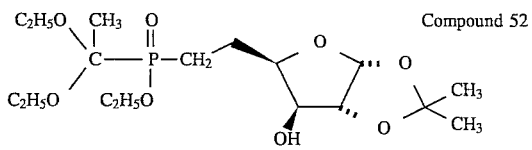

Compound 52

To a solution of ethylmethyl(1,1-diethoxyethyl)phosphinate (1.55 g, 6.9 mmole) in THF (30 ml) at −78° C. under an atmosphere of argon is added n butyllithium (4.3 ml, 1.6 molar solution in hexanes) slowly over 5 minutes. The resulting solution is stirred at −78° C. for 1 hour. Boron trifluoride etherate (0.85 ml, 6.9 mmole) is then added over 2 minutes followed by the dropwise addition of a solution of an oxetane of formula

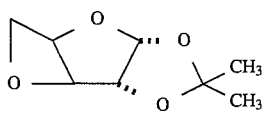

prepared by the method of: J. P. Horwitz et al J. Org. Chem. 28,942, (1963) (0.40 g, 2.3 mmole) in THF (10 ml). The resulting solution is stirred for 2 hours at −78° C. before the addition of NaHCO$_3$ (saturated, 5 ml). The resulting mixture is allowed to warm to ambient temperature over 1 hour and is then concentrated in vacuo. Addition of dichloromethane and filtration gives a clear oil after concentration. Purification by flash silica column chromatography (chloroform-ethanol 40:1) gives Compound 52 as a thick oil.

Found: C 50.6%, H 8.4%, P 7.7%; C$_{17}$H$_{33}$O$_8$P.½H$_2$O requires C 50.35%, H 8.45%, P 7.65%.

$^{31}$P nmr $^1$H decoupled (CDCl3, 36.4 MHz) δ51.3, 51.1 ppm.

Example 51

This describes the preparation of a mixture of

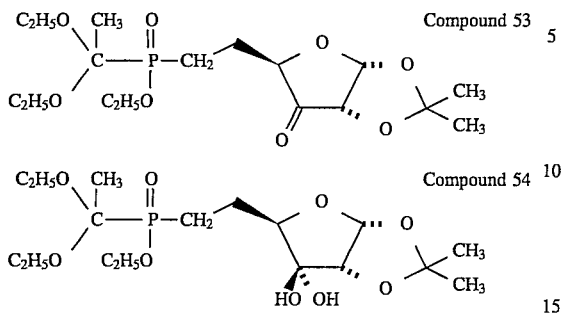

A solution of dimethylsulphoxide (0.56 ml, 7.9 mmol) in dichloromethane (5 ml) is added to a mixture of oxalyl chloride (0.3 ml, 3.4 mmol) in dichloromethane (45 ml) maintained at −70° C. After 10 minutes, a solution of Compound 52 (1.05 g, 2.64 retool) in tetrahydrofuran (10 ml) is added dropwise, maintaining the temperature at −70° C. After 15 minutes, triethylamine (2.76 ml, 0.0198 mol) is added dropwise and the mixture is allowed to warm gradually to ambient temperature. The mixture is diluted with ethyl acetate (150 ml) and washed with water (2×50 ml). Evaporation of the organic phase and co-evaporation with more ethyl acetate gives a mixture of Compounds 53 and 54 as a colourless oil which is pure enough for use in subsequent reactions. A sample (80 mg) is purified by column chromatography over silica gel (Merck, Art 7734, 3 g) eluting with dichloromethane: ethyl acetate (25:1) mixtures. Pure fractions are evaporated to give a mixture of Compounds 53 and 54 as a colourless oil.

ν max (thin film) 3600–3100 (br, OH), 1780, 1740 (CO) cm$^{-1}$ $^{31}$P nmr (CDCl$_3$) δ52.01, 51.72 and 48.30, 48.01 ppm.

Example 52

This describes the preparation of

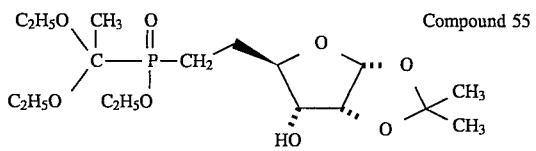

To a solution of the mixture of Compounds 53 and 54 obtained in Example 51 (1.02 g, 2.485 mmol) in ethanol (50 ml) at −10° C. is added sodium borohydride (113 mg, 2.98 mmol) in three portions over 15 minutes. The mixture is partitioned between ethyl acetate (200 ml) and water (50 ml). The organic phase is washed with water (2×5 ml), dried (MgSO$_4$), filtered and evaporated to yield Compound 55 as a colourless oil.

$^{31}$P (CDCl$_3$) δ49.32 ppm.

$^1$H nmr (CDCl$_3$) δ5.76 (1H, d, H-1), 4.58 (1H, m, H-2$^1$), 4.2 (2H, m, H-3, H-4), 3.7 (6H,m, OCH$_2$×3), 3.05 (1H, br d, OH), 2.15–1.7 (4H, m, PCH$_2$CH$_2$), 1.58 and 1.35 (2×s, 2×OC(CH$_3$)$_2$), 1.44 (3H, d, PCCH$_3$), 1.35 and 1.25 (6H, 2×t, OCH$_2$CH$_3$), 1.20 (6H, t, P COCH$_2$CH$_3$×2)ppm.

Example 53

This describes the preparation of

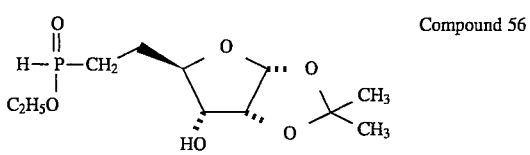

To a solution of Compound 55 (0.97 g, 2.447 mmol) in chloroform (35 ml) containing 0.6% ethanol at room temperature, under argon is added trimethylsilyl chloride dropwise over 30 minutes. The mixture is stirred at 24° C. for 6 hours, then kept at −20° C. for 18 hours. Evaporation gives crude product (780 mg) as a colourless oil. Purification by column chromatography over silica gel (Merck, Art 7734, 35 g) eluting with 1–8% ethanol: chloroform mixtures. Appropriate fractions are collected and evaporated to give Compound 56 as a colourless oil.

$^{31}$P nmr (CDCl$_3$) δ38.90 and 38.64 ppm.

$^1$H nmr (CDCl$_3$) δ7.80 (0.5H, m, P—H), 6.43 (0.5H, m, P—H), 5.75 (1H, m, H-1), 4.48 (1H, m, H-4), 4.15 (1H, m, POCH), 4.08 (1H, m, POCH), 3.61 (1H, m, H-3), 2.1–1.8 (4H, m, P CH$_2$CH$_2$), 1.55 (3H, s, CCH$_3$), 1.35 (6H, m, CCH$_3$ and POCH$_2$CH$_3$) ppm.

$^{13}$C nmr (CDCl$_3$) 112.47 (s), 103.54 (s), 79.30(d), 78.54 (s), 75.29 (s), 62.36 (s), 26.38 (s), 26.28 (s), 24.71 (d), 16.210 (s) ppm.

Example 54

This describes an alternative preparation of

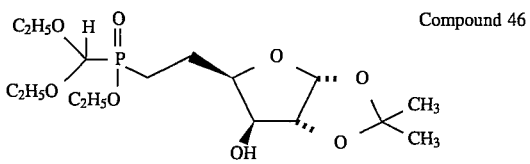

To a solution of ethylmethyl(diethoxymethyl)phosphinate (1.83 g, 8.7 mmole) in THF (30 ml) at −78° C. under an atmosphere of argon is added n-butyllithium (5.43 ml, 1.6 molar solution in hexanes) slowly over 5 minutes. The resulting solution is stirred at −78° C. for 1 hour. Boron trifluoride etherate (1.06 ml, 8.6 mmole) is then added rapidly followed by the dropwise addition of a solution of the oxetane used in Example 50 (0.50 g, 2.9 mmole) in THF (10 ml) over 10 minutes. The resulting solution is stirred at −78° C. for 1½ hours before the addition of NaHCO$_3$ (saturated, 2 ml) and slow warming to ambient temperature. Concentration under vacuum, addition of CH$_2$Cl$_2$ (100 ml), filtration and reconcentration gives a colourless oil. Purification by flash silica column chromatography (chloroform-ethanol 35:1) gives Compound 46 as a thick oil.

$^{31}$P nmr $^1$H decoupled (CDCl$_3$, 36.4 MHz) δ47.4, 47.3 ppm.

Example 55

This describes the preparation of

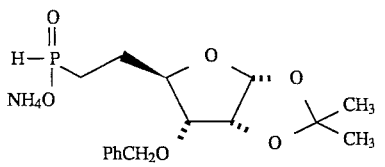
Compound 57 where Ph is phenyl.

To a solution of aqueous ammonia (20 ml, 20%) Compound 38 (0.95 g, 2.1 mmol) is added. The mixture is heated at 70° C. for 12 hours, cooled, evaporated and then co-evaporated with toluene to give Compound 57.

Example 56

This describes the preparation of

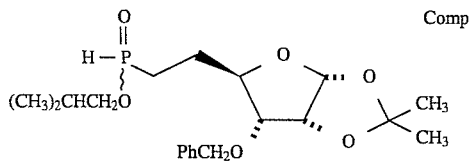
Compound 58 where Ph is phenyl.

All of Compound 57 obtained in Example 55 is dissolved in dichloromethane (9 ml). To the resulting solution at −10° C. is added triethylamine (0.32 ml, 2.3 mmol), followed dropwise by isobutyl chloroformate (0.55 ml, 4.2 mmol). After 45 minutes, the reaction mixture is allowed to warm to 20° C. After 2 hours, the reaction mixture is evaporated and the residue purified by chromatography on silica gel, eluting with a gradient of methanol/ethyl acetate. The product, a mixture of two diastereoisomers, is obtained as a clear oil.

$^{31}$P nmr (36 MHz, CDCl$_3$) δ38.8, 39.1 ppm; J$_{PH}$540 Hz.
m/z CI(NH$_3$) 399(MH$^+$), 416 (MNH$_4^+$), 341 (100) (M-iBu).

Example 57

This describes the preparation of

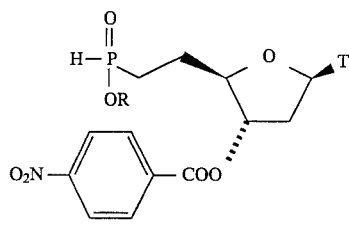

Compound 59 (R = H)

Compound 60 (R = (CH$_3$CH$_2$)$_3^+$NH)

To a solution of Compound 7 (1.5 g, 3.1 mmol) in dichloromethane (16 ml) at −70° C., is added bromotrimethylsilaine (0.44 ml, 3.4retool). The solution is allowed to warm to 0° C., then cooled again to −70° C. Further bromotrimethylsilane (0.88 ml, 6.8 mmol) is added and the mixture is maintained at −18° C. for 48 hours. Methanol is added, and the mixture is evaporated to give Compound 59, which is purified by passing through a column of ion exchange resin, eluting with water, then a methanol/water gradient.

Triethylamine is added to Compound 59 and the mixture is evaporated to give Compound 60, the triethylammonium salt.

$^{31}$Pnmr (162 MHz, CDCl$_3$) δ25.2 ppm; J$_{PH}$495 Hz
m/z (FAB$^+$) 555 (MH$^+$).

Example 58

This example describes the preparation of

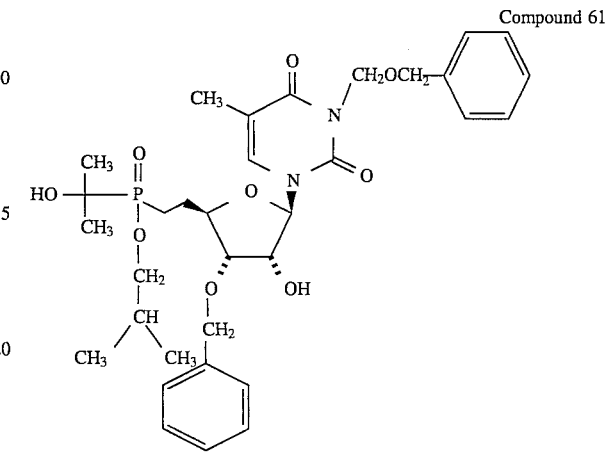
Compound 61

Compound 42 (16.79 g., 32 mmole) is dissolved in dichloromethane (100 ml) and the mixture is cooled to 5° C. 1,8-Diazabicyclo [5.4.0]undec-7-ene (DBU) (10.72 g., 70.4 mmole) is added followed by phenylmethoxychloromethane (6.02 g., 38.4 mmole). The reaction mixture is allowed to warm to room temperature and stirred for three hours. Further phenylmethoxychloromethane (0.6 g, 3.8 mmole) is added and the mixture left overnight. Dilute hydrochloric acid (100 ml) is added and the organic phase separated off and washed with water then brine and dried (MgSO$_4$). Evaporation of the solvent gives an oil which is purified by dry flash silica chromatography using 2% methanol in dichloromethane as eluant to give Compound 61.

$^{31}$Pnmr (CDCl$_3$, 162 MHz) δ55.87 ppm.

Example 59

This describes the preparation of

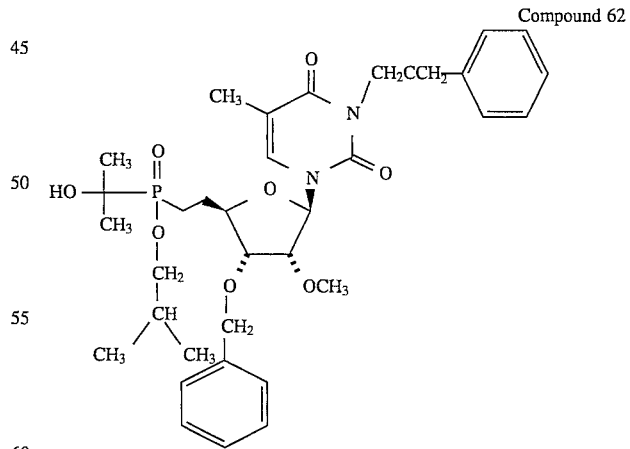
Compound 62

Compound 61 (5.6 g, 8.7 mmole, and iodomethane (2.47 g, 8.7 mmole) are stirred in acetonitrile (50 ml) and the solution is cooled to 5° C. 2-tert-Butylimino-2-diethylamino-1, 3-dimethylperhydro 1,3,2-diazaphosphorin-BDDDP., ex Fluka (2.38 g., 8.7 mmole) is added and the mixture stirred for 5 hours. More iodomethane (1.2 g) and BDDDP (1.2 g) are added in portions over 24 hours. The solvent is removed by evaporation and the residue dissolved in ethyl acetate and washed successively with water, dilute HCl, aqueous NaHCO$_3$ and brine. The solvent is removed and the residue is purified by flash chromatography using 10% methanol in chloroform eluant on silica, and then silica chromatography using 1.2% methanol in chloroform as eluant. There is obtained Compound 62.

$^{31}$Pnmr (CDCl$_3$ 162 MHz) δ55.78 ppm.

Example 60

This example describes the preparation of

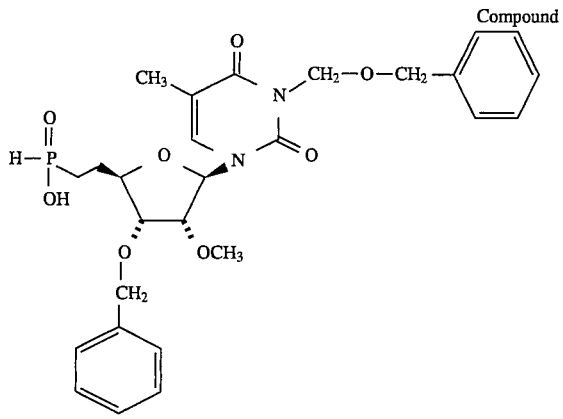

Compound 63

A solution of Compound 62 (1.3 g., 1.97 mmole) in methanol (10 ml) and aqueous ammonia (50%, 25 ml) is heated at 80° C. for 8 hours. The resulting solution is evaporated and the residual oil dissolved in water (10 ml). Dowex (50WX2) ion exchange resin is added until the solution becomes acidic. The Dowex is filtered off and the aqueous solution evaporated to dryness to give Compound 63.

$^{31}$Pnmr (CD$_3$OD., 162 MHz) δ35.89 ppm., $J_{PH}$540 Hz

Example 61

This example describes the preparation of

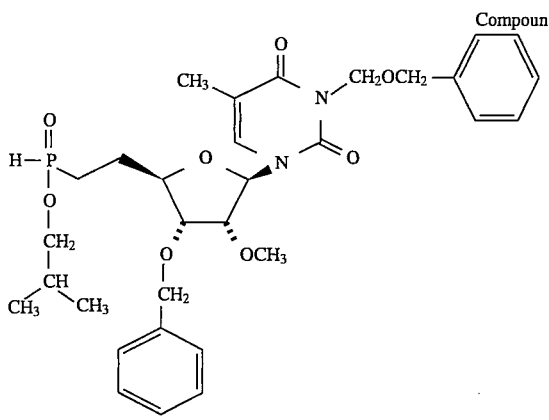

Compound 64

Compound 63 (0.45 g., 0.83 mmole) is dissolved in tetrahydrofuran (5 ml.) and 2-methylpropan-1-ol (0.07 g., 0.99 mmole), dimethylaminopyridine (50 mg. ), and dicyclohexylcarbodiimide (0.205 g., 0.99 mmole) are added. The mixture is stirred for three hours. Ether (1 5 ml.) and hexane (5 ml.) are added, the dicylohexylurea formed is filtered off and the solvent is evaporated. The residual oil is purified by chromatography on silica using 2% methanol in ethyl acetate as eluant, to give Compound 64.

$^{31}$Pnmr. (CDCl$_3$ 162 MHz) δ38.29 and 38.75 ppm, $J_{PH}$= 540 Hz

Example 62

This example describes the preparation of

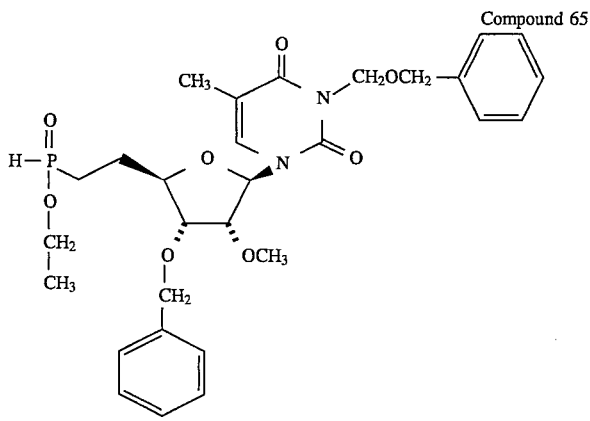

Compound 65

Compound 63, (0.9 g, 1.65 mmole) is dissolved in tetrahydrofuran (10 ml.) and ethanol (0.076 g., 1.65 mmole), Dimethylaminopyrine (10 mg.), and dicyclohexylcarbodiimide (0.409 g., 1.98 mmole) are added and the mixture is stirred for three hours. Ether (30 ml.) and hexane (5 ml.) are added and the dicyclohexyl urea formed is filtered off. Evaporation of the solvent gives Compound 65.

$^{31}$Pnmr(CDCl$_3$, 162 MHz) δ37.65, 38.09 ppm, $J_{PH}$=535 Hz

Example 63

This example describes the preparation of

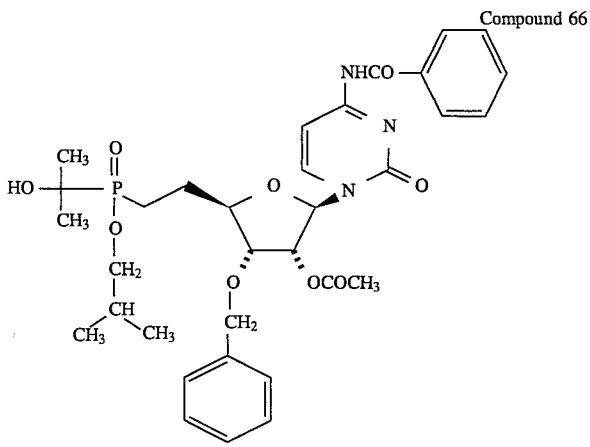

Compound 66

N-Benzoylcytosine (3.4 g., 15.88 mmole) N,O-bis trimethylsilylacetamide (9.69 g., 47.65 mmole) and dichloroethane (40 ml) are stirred at 50° C. for 1 hour. The resulting clear solution is cooled to room temperature and Compound 40 (7.95 g., 15.88 mmole) in dichloroethane (40 ml.) is added, followed by trimethylsilyltrifluoromethane sulphonate (10.6 g., 47.65 mmole). The mixture is stirred at 50° C. for 4 hours, then cooled and poured onto ice-cold saturated aqueous sodium bicarbonate maintaining pH above 7. The organic phase is separated, washed with brine and dried. On evaporation of the solvent, a yellow foamy solid is obtained. This is dissolved in acetic acid (60 ml.), THF (20 ml.) and water (20 ml.). The solution is heated to 50° C. for four hours. The resulting mixture is evaporated to half the volume and then co-evaporated with methanol and water mixtures twice. There is obtained Compound 66 as a white solid, which is further purified by chromatography on silica using 10% methanol in chloroform as eluant.

$^{31}$Pmnr. (CDCl$_3$, 162 MHz) δ54.7, 54.8 ppm.

Example 64

This example describes the preparation of

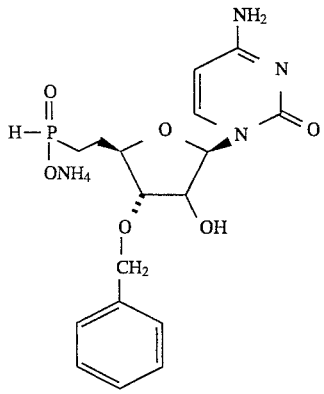

Compound 67

Compound 66 (2.0 g., 3.0 mmole), sodium methoxide (0.65 g., 25% solution in methanol) and methanol (20 ml) are mixed. The mixture is left at room temperature overnight under argon. Dowex 50WX8 H$^+$ form ion exchange resin is added until the solution is acidic. The Dowex is filtered off and washed with methanol and water, then eluted with aqueous ammonia (1%). Evaporation of the eluant gives Compound 67.

$^{31}$Pnmr (CD$_3$OD, 162 MHz) δ27.5 ppm. $J_{PH}$=500 Hz.

Example 65

This example describes the preparation of

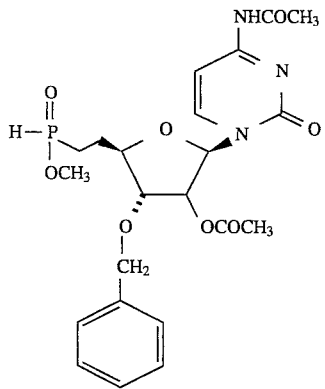

Compound 68

Compound 67 (0.08 g.), acetic anhydride (2 ml.), pyridine (2 ml.) and tetrahydrofuran (5 ml) are heated at 50° C. for 3 hours. The mixture is evaporated and co-evaporated with methanol (3×10 ml.). The residue is purified by silica chromatography using 5% methanol in chloroform as eluant. There is obtained Compound 68 as a colourless oil.

$^{31}$Pnmr (CDCl$_3$, 160 MHz) δ=40.84., 41.16 ppm. $J_{PH}$= 540 Hz

Example 66

This describes the preparation of

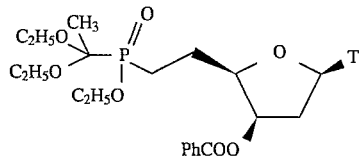

Compound 69 where Ph is phenyl and T is 1-thyminyl.

To a solution of Compound 1 (6.08 g, 13.6 mmol) in dry pyridine (50 ml) is added benzoyl chloride (1.89 ml, 16.3 mmol). After standing at room temperature under argon for 48 hours, concentration gives a yellow oil. Dissolution in dichloromethane (200 ml), washing with 0.5N HCl (2×50 ml) and saturated NaHCO$_3$ (2×50 ml) and drying over Na$_2$SO$_4$ gives a yellow foam which is purified by repeated flash silica column chromatography to give Compound 69 as a white solid.

$^{31}$P nmr $^1$H decoupled (CDCl$_3$, 162 MHz) δ48.3 and 48.2 ppm m/z (CI, NH$_3$) 553.3 (MH$^+$)

Example 67

This describes the preparation of

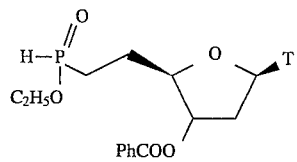

Compound 70 where Ph is phenyl and T is 1-thyminyl.

Trimethylsilylchloride (1.6 ml, 13 mmole) is added to a stirred solution of Compound 69 (700 mg, 1.3 mmole) in chloroform (10 ml) containing ethanol (0.2 ml) under argon. The resulting solution is stood at room temperature for 20 hours and is then concentrated under vacuum. Purification by flash silica column chromatography (eluant:chloroform/ethanol 20:1) gives Compound 70 as a white foam isolated as a mixture of 2 diastereoisomers.

Found C 52.4, H5.4, N 6.2, P 6.3%;

C$_{20}$H$_{25}$N$_2$O$_7$P.¼CHCl$_3$ requires C52.15, H5.45, N6.0, P6.65%.

m/z (CI NH$_3$) 454(MNH$_4^+$)437(MH$^+$)

Example 68

This describes the preparation of

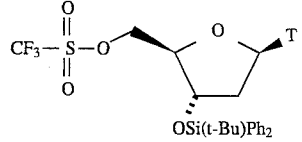

Compound 71 where t-Bu is tertiary butyl, Ph is phenyl and T is 1-thyminyl.

To a solution of pyridine (0.34 ml, 4.2 mmol) in dichloromethane (30 ml), under argon at −10° C., is added trifluoromethane sulphonic anhydride (0.46 ml, 2.7 mmol) dropwise over 10 minutes. The resulting suspension is stirred at −10° C. for 10 minutes and then cooled to −20° C. A solution of 3'-t-butyldiphenyl silyloxy deoxythymidine (H. Köster and N. D. Sinha, Tetrahedron Lett. 1982, 23, 2641) (1.0 g, 2.1 mmol) in dichloromethane (10 ml) is added dropwise. After completion of addition the resulting mixture is stirred at −20° C. for 1 hour. The mixture is quenched by the addition of ice and water and the organic phase separated, dried (Na$_2$SO$_4$), filtered and evaporated to give Compound 71 as a pink foam which is used crude in subsequent Examples.

$^1$H nmr (CDCl$_3$, 400 MHz) δ9.50 (1H, brs, NH), 7.63 (4H,m, ortho Ph), 7.47 (2H,m, para Ph), 7.41 (4H,m, meta Ph), 7.06 (1H,d, J1 Hz,H6), 6.43 (1H,dd, J8 and 6 Hz, H1$^1$), 4.40 (1H,ddd,J6,3 and 3 Hz, H3$^1$), 4.32 (1H,dd,J11 and 2 Hz,H5$^1$), 4.03 (1H,ddd,J3,3 and 3 Hz,H4$^1$), 3.69 (1H,dd,J11 and 3 Hz, H5$^1$), 2.44 (1H,ddd, J14, 6 and 3 Hz,H2$^1$), 1.97 (1H,ddd, J14, 8 and 8 Hz, H2$^1$), 1.86(3 H,d,J1 Hz, C$_5$—CH$_3$), 1.10(9H,s,tBu)ppm.

Example 69

This describes the preparation of

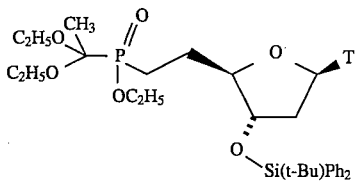
Compound 72 where t-Bu is tertiary butyl, Ph is phenyl and T is I-thyminyl.

To a solution of ethyl methyl (1,1-diethoxyethyl) phosphinate (0.365 g, 1.63 mmol) in THF (10 ml) under argon at −78° C. is added butyllithium (1.02 ml, 1.6 molar solution in hexanes). The resulting solution is stirred at −78° C. for 1 hour. A solution of Compound 71 (0.20 g, 0.32 mmol) in THF (5 ml) is then added dropwise over 20 minutes. After stirring for a further 1 hour at −78° C., saturated ammonium chloride solution (3 ml) is added and the solution warmed to room temperature. Extraction of the mixture with chloroform (3×20 ml), drying (magnesium sulphate) and concentration gives the crude product, which is purified by Kugelrohr distillation (100° C., 0.1 mmHg) to remove relatively volatile components followed by flash silica column chromatography (eluant THF:toluene, 3:1) to give Compound 72.

$^{31}$P nmr $^1$H decoupled (CDCl$_3$, 162 MHz) δ48.9 and 48.7 ppm.

Example 70

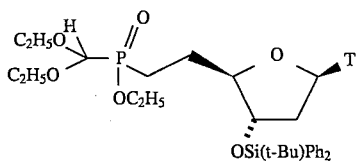
Compound 73 where t-Bu is tertiary butyl, Ph is phenyl and T is I-thyminyl.

To a solution of ethyl methyl (1,1-diethoxymethyl) phosphinate (0.34 g, 1.62 mmol) in THF (10 ml) under argon at−78° C. is added n-butyllithium (1.02 ml, 1.6 molar solution in hexanes). The resulting solution is stirred at −78° C. for 1 hour. A solution of Compound 71—(0.2 g, 0.32 mmol) in THF is then added dropwise over 20 minutes. After stirring for a further 1 hour at −78° C., saturated ammonium chloride solution (3 ml) is added. After warming to room temperature, the mixture is extracted with chloroform (3×20 ml) and dried (MgSO$_4$). Concentration and purification by flash silica column chromatography (eluant chloroform-ethanol 30:1), Kugerlrohr distillation (0.8 mmHg, 88° C.) to remove residual volatiles and further flash silica column chromatography (THF: toluene, 2:1) gives Compound 73.

$^{31}$P nmr $^1$H decoupled (CDCl$_3$, 162 MHz) δ45.85, and 45.80 ppm.

What is claimed is:

1. A compound of formula

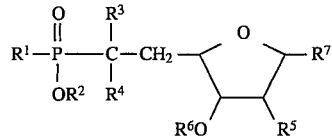

where

R$^1$ is hydrogen or Q, wherein Q is a protecting group;

R$^2$ is hydrogen, a C$_1$–C$_8$ aliphatic radical, a C$_6$–C$_{15}$ aromatic radical, a C$_3$–C$_8$ cycloaliphatic radical, a C$_7$–C$_{13}$ araliphatic radical, an alkali metal ion or an ammonium ion;

R$^3$ and R$^4$ are independently hydrogen, halogen or hydroxy;

R$^5$ is C$_6$–C$_{10}$ aryloxythiocarbonyloxy, the C$_6$–C$_{10}$ aryl group being unsubstituted substituted, or R$^5_a$;

R$^5_a$ is hydrogen, fluorine, chlorine, hydroxy. —OR$^8$, —OCOR$^8$ or silyloxy substituted by three C$_1$–C$_{15}$ hydrocarbyl groups;.

R$^6$ is hydrogen, a C$_1$–C$_{10}$ aliphatic radical. a C$_6$–C$_{15}$ aromatic radical, a C$_7$–C$_{16}$ araliphatic radical, —COR$^9$, —SO$_2$R$^9$ or silyl substituted by three C$_1$–C$_{15}$ hydrocarbyl groups;

R$^7$ is a monovalent nucleoside base radical, hydroxyl, —OR$^8$ or —OCOR$^8$, and R$^8$ and R$^9$ are independently a C$_1$–C$_{10}$ aliphatic radical, a C$_3$–C$_8$ cycloaliphatic radical, a C$_6$–C$_{15}$ aromatic radical or a C$_7$–C$_{16}$ araliphatic radical; or R$^5$ and the indicated R$^6$O— together denote an isopropylidenedioxy group or R$^5$ and R$^7$ together denote an isopropylidenedioxy group, provided that when R$^5$ and R$^7$ together denote an isopropylidenedioxy group, R$^1$, R$^2$, R$^3$, R$^4$ and R$^6$ are not all hydrogen.

2. A compound of claim 1, in which R$^2$ is hydrogen, substituted or unsubstituted C$_1$–C$_8$ alkyl, C$_3$–C$_8$ cycloalkyl, C$_6$–C$_{15}$ aryl or C$_7$–C$_{13}$ aralkyl, an alkali metal ion or an ammonium ion;

R$^5$ as R$^5_a$ is hydrogen, fluorine, chlorine, hydroxy, C$_1$–C$_{10}$ alkoxy, C$_2$–C$_{10}$ alkenoxy, C$_6$–C$_{15}$ aryloxy, C$_7$–C$_{16}$ aralkyloxy, —OCOR$^8$ or silyloxy substituted by three C$_1$–C$_{15}$ hydrocarbyl groups;

R$^6$ is hydrogen, substituted or unsubstituted C$_1$–C$_{10}$ alkyl, C$_2$–C$_{10}$ alkenyl, C$_6$–C$_{15}$ aryl or C$_7$–C$_{16}$ aralkyl, —COR$^9$, —SO$_2$R$^9$ or silyl substituted by three C$_1$–C$_{15}$ hydrocarbyl groups; and R$^8$ and R$^9$ are independently substituted or unsubstituted C$_1$–C$_{10}$ alkyl, C$_2$–C$_{10}$ alkenyl, C$_3$–C$_8$ cycloalkyl, C$_6$–C$_{15}$ aryl or C$_7$–C$_{16}$ aralkyl.

3. A compound of claim 1, which is a stereoisomer of formula

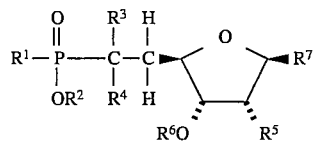

4. A compound of claim 1, in which the protecting group Q is of formula

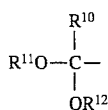

II where $R^{10}$ is hydrogen, $C_1$–$C_{10}$ alkyl, $C_3$–$C_8$ cycloalkyl, $C_6$–$C_{10}$ aryl or $C_7$–$C_{11}$ aralkyl and $R^{11}$ and $R^{12}$ are independently $C_1$–$C_{10}$ alkyl; or the protecting group Q is of formula

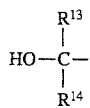

III where $R^{13}$ and $R^{14}$ are independently $C_1$–$C_{10}$ alkyl or $R^{13}$ is $C_1$–$C_{10}$ alkyl and $R^{14}$ is $C_6$–$C_{10}$ aryl.

5. A compound of claim 4, in which $R^{10}$ is hydrogen or $C_1$–$C_4$ alkyl, $R^{11}$ and $R^{12}$ are each $C_1$–$C_4$ alkyl and $R^{13}$ and $R^{14}$ are each $C_1$–$C_4$ alkyl.

6. A compound of claim 1, in which $R^2$ is hydrogen, unsubstituted or substituted $C_1$–$C_6$ alkyl or an unsubstitued or substituted ammonium ion.

7. A compound of claim 1, in which $R^3$ and $R^4$ are each hydrogen.

8. A compound of claim 1, in which $R^5$ is hydrogen, hydroxy, $C_1$–$C_4$ alkoxy, —$OCOR^8$ where $R^8$ is $C_1$–$C_{10}$ alkyl, or $C_1$–$C_4$ alkyl- or halogen-substituted phenyloxythiocarbonyloxy, or $R^5$ together with $R^7$ denotes an isopropylidenedioxy group or $R^5$ together with $R^6O$— denotes an isopropylidenedioxy group; $R^6$ is hydrogen, $C_7$–$C_9$ aralkyl, —$COR^9$ or —$SO_2R^9$ where $R^9$ is unsubstituted or substituted $C_1$–$C_4$ alkyl or $C_6$–$C_{10}$ aryl, $C_1$–$C_6$ alkyldi ($C_6$–$C_8$ aryl) silyl or $R^6$ together with the attached oxygen atom and $R^5$ denotes an isopropylidenedioxy group; and $R^7$ is hydroxy, —$COR^8$ where $R^8$ is $C_1$–$C_{10}$ alkyl or an unsubstituted or substituted thyminyl, cytosinyl, guaninyl or adeninyl group, or $R^7$ together with $R^5$ denotes an isopropylidenedioxy group.

9. A compound of claim 4, in which $R^1$ is hydrogen or a protecting group Q of formula II as defined in claim 4, in which $R^{10}$ is hydrogen, or methyl and $R^{11}$ and $R^{12}$ are each ethyl; $R^2$ is hydrogen, methyl or ethyl; $R^3$, $R^4$ and $R^5$ are each hydrogen; $R^6$ is hydrogen, —$COR^9$ where $R^9$ is phenyl, 4-nitrophenyl or alpha-naphthyl, —$SO_2R^9$ where $R^9$ is methyl or p-tolyl, or tert-butyldiphenylsilyl; and $R^7$ is thyminyl or N-(4-nitrobenzoyl)thyminyl; or $R^5$ and $R^7$ together denote an isopropylidenedioxy group; or $R^1$ is hydrogen or a protecting group of formula III as defined in claim 4, in which $R^{13}$ and $R^{14}$ are each methyl; $R^2$ is hydrogen, methyl, ethyl, isobutyl, ammonium or triethylammonium; $R^3$ and $R^4$ are each hydrogen; $R^5$ is hydrogen, hydroxy, methoxy, —$OCOCH_3$ or p-tolyloxythiocarbonyloxy, $R^6$ is hydrogen, benzyl or —$COR^9$ where $R^9$ is methyl or 4-nitrophenyl; and $R^7$ is hydroxy, —$OCOCH_3$, thyminyl, N-benzyloxymethylthyminyl, cytosinyl,N-acetylcytosinyl, N-benzoylcytosinyl, guaninyl, adeninyl or N-benzoyladeninyl; or $R^8$ and $R^7$ together denote an isopropylidenedioxy group, or $R^5$ together with $R^6O$— denotes an isopropylidenedioxy group.

10. A pharmaceutical composition, which comprises an effective antiviral amount of a compound of claim 1 and a pharmaceutically acceptable carrier.

* * * * *